(12) United States Patent
Dutta et al.

(10) Patent No.: US 6,890,743 B2
(45) Date of Patent: May 10, 2005

(54) GEMININ AND ORC3N INHIBIT REPLICATION OF HERPESVIRUSES, PAPILLOMAVIRUSES, AND POLYOMAVIRUSES

(75) Inventors: Anindya Dutta, Brighton, MA (US); Suman K. Dhar, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 10/178,055

(22) Filed: Jun. 21, 2002

(65) Prior Publication Data

US 2003/0105008 A1 Jun. 5, 2003

Related U.S. Application Data

(60) Provisional application No. 60/299,963, filed on Jun. 21, 2001.

(51) Int. Cl.[7] .................................................. C12P 19/34
(52) U.S. Cl. ...................... 435/91.33; 435/6; 435/320.1; 530/300
(58) Field of Search ....................... 435/6, 91.33, 320.1; 530/300

(56) References Cited

U.S. PATENT DOCUMENTS

| | | |
|---|---|---|
| 5,589,341 A | 12/1996 | Stillman et al. |
| 5,614,618 A | 3/1997 | Stillman et al. |
| 5,851,821 A | 12/1998 | Williams et al. |
| 6,074,819 A | 6/2000 | Stillman et al. |

FOREIGN PATENT DOCUMENTS

| | | | |
|---|---|---|---|
| WO | WO 99/58673 | * | 11/1999 |
| WO | WO 99/58673 A1 | | 11/1999 |
| WO | WO 00/44900 A2 | | 8/2000 |
| WO | WO 00/60078 A2 | | 10/2000 |
| WO | WO 01/98489 A1 | * | 12/2001 |

OTHER PUBLICATIONS

Garson et al. The Lancet, Jan. 1998, vol. 351, No. 9095.*
Dhar, S. K. et al., Identification and Characterization of the Human ORC6 Homolog. J. of Biol Chem 275(45): 34983–34988, 2000.
Dunn, M. J. et al., Detection of proteins in polyacrylamide gels using an ultrasensitive silver staining technique. Method Mol Biol 32: 113–118, 1994.
Dutta, A. et al., Initiation of DNA Replication in Eukaryotic Cells, Annu Rev. Cell Dev. Biol 13:293–332, 1997.
Frappier, L. et al., Overproduction, Purifcation and Characterization of EBNA1, the Origin Binding Protein of Epstain–Barr Virus. J. of Biol. Chem 266: 7819–7826, 1991.
Gahn, T. A. et al., The Epstein–Barr virus origin of plasmid replication, oriP, contains both the initiation and termination sites of DNA replication. Cell 58: 527–535, 1989.
Gavin, K. A. et al., Conserved Initiator Proteins in Eukaryotes. Science 270: 1667–1671, 1995.

Gilbert, D. M. et al., Mimosine Arrests DNA Synthesis at Replication Forks by Inhibiting Beoxyribinucleotide Metabolism. J Biol Chem 270(16): 9597–9606, 1995.
Harrison, S. et al., Sequence Requirements of the Epstein–Barr virus (EBV) oriP–based episomes requires EBV–encoded nuclear antigen–1 chromosome–binding domains, which can be replaced by high–mobility group–1 or histone H1. Proc. Natl. Acad. Sci. USA 98(4): 1865–1870, 2001.
Hung, S. C. et al., Maintenance of Epstein–Barr virus (EBV) oriP–based episomes requires EBV–encoded nuclear antigen–1–chromosome–binding domains, which can be replaced by high–mobility group–1 or histone H1. Proc Natl Acad Sci USA 98(4): 1865–1870, 2001.
Krysan, P. J. et al., Isolation of Human Sequences That Replicate Autonomously in Human Cells. Mol. Cell Biol 9(3): 1026–1033, 1989.
Lin, Y.L. et al., Dissection of Functional Domains of the Human DNA Replication Protein Complex Replication Protein A. J Biol Chem 271(29): 17190–17198, 1996.
Marechal, V. et al., Mapping EBNA–1 Domains Involved in Binding to Metaphase Chromosomes. J. Virol 73(5): 4385–4392, 1999.
Mayer, B.J. et al., Evidence that SH2 domains promote processive phosphorylation by protein–tyrosine kinases. Curr. Biol. 5(3): 296–305, 1995.
McGarry, T. J. et al., Geminin, an Inhibitor of DNA Replication, Is Degraded during Mitosis. Cell 93: 1043–1053, 1998.
Middleton, T. et al., EBNA1 Can Link the Enhancer Element to the Initiator Element of the Epstein–Barr Virus Plasmid Origin of DNA Replication. J. Virol. 66(1): 489–495, 1992.
Pinto, S. et al., *latheo* Encodes a Subunit of the Origin Recognition Complex and Disrupts Neuronal Proliferation and Adult Olfactory Memory When Mutant. Neuron 23: 45–54, 1999.
Quintana, D. G. et al., Identification of HsORC4, a Member of the Human Origin of Replication Recognition Complex. J Biol Chem 272(45): 28247–28251, 1997.
Quintana, D. G. et al., ORC5L, a New Member of the Human Origin Recognition Complex, Is Deleted in Uterine Leiomyomas and Malignant Myeloid Diseases. J. Biol Chem 273(42): 27137–27145, 1998.

(Continued)

Primary Examiner—Ali R. Salimi
(74) Attorney, Agent, or Firm—Wolf, Greenfield & Sacks, P.C.

(57) ABSTRACT

The invention relates to the use of geminin and/or Orc3N molecules for inhibiting viral replication. Use of the molecules and related molecules in the prevention and treatment of viral infections, such as papillomavirus infections, polyomavirus infections, and herpesvirus infections, such as Epstein-Barr virus (EBV) infections, are described.

10 Claims, 13 Drawing Sheets

OTHER PUBLICATIONS

Romano, G. et al., Latest Developments in Gene Transfer Technology: Achievements, Perspectives, and Controversies, Over Therapeutic Applications. Stem Cells 18: 19–39, 2000.

Simpson, K., et al., Stable Episomal Maintenance of Yeast Artificial Chromosomes in Human Cells. Mol Cell Biol 16: 5117–5126, 1996.

Somia, N. et al., Gene Therapy: Trials and Tribulations. Nat Rev Genet 1: 91–99, 2000.

Sverdrup, F.M. et al., Development of human papillomavirus plasmids capable of episomal replication in human cell lines. Gene Therapy 6: 1317–1321, 1999.

Tatsumi, Y. et al., Association of Human Origin Recognition Complex 1 with Chromatin DNA and Nuclease–resistant Nuclear Structures. J Biol Chem 275(8): 5904–5910, 2000.

Thome, K. C. et al., Subsets of Human Origin Recognition Complex (ORC) Subunits Are Expressed in Non–proliferating Cells and Associate with Non–ORC Proteins. J Biol Chem 275(45): 35233–35241, 2000.

Tugal, T. et al., The Orc4p and Orc5p Subunits of the *Xenopus* and Human Origin Recognition Complex Are Related to Orc1p and Cdc6p. J Biol Chem 273(49): 32421–32429 1998.

Waldman, T., et al., p21 Is Necessary for the p53–mediated $G_1$ Arrest in Human Cancer Cells. Cancer Res 55: 5187–5190, 1995.

Wohlschlegel, J. A. et al., Inhibition of Eukaryotic DNA Replication by Germinin Binding to Cdt1. Science 290: 2309–2312, 2000.

Wysokenski, D. A. et al., Multiple EBNA1–Binding Sites are Required To Form an EBNA1–Dependent Enhancer and To Activate a Minimal Replicative Origin Within *oriP* of Epstein–Barr Virus. J Virol 63(6): 2657–2666, 1989.

Yates, J. L. et al., Dissection of DNA Replication and Enhancer Activation Functions of Epstein–Barr Virus Nuclear Antigen 1. Cancer Cells 6: 197–205, 1988.

Yates, J. L. et al., Epstein–Barr Virus–Derived Plasmids Replicate Only Once per Cell Cycle and Are Not Amplified after Entry into Cells. J Virol 65(1): 483–488, 1991.

Yates, J. L., et al., Stable replication of plasmids derived from Epstein–Barr virus in various mammalian cells. Nature 313: 812–815, 1985.

Yates, J. L. et al., The Minimal Replicator of Epstein–Barr Virus *oriP*. J Virol 74(10): 4512–4522, 2000.

\* cited by examiner

A

B

C

D

GEMININ AND ORC3N INHIBIT REPLICATION OF HERPESVIRUSES, PAPILLOMAVIRUSES, AND POLYOMAVIRUSES

RELATED APPLICATIONS

This application claims priority under 35 U.S.C. §119 from U.S. provisional application Ser. No. 60/299,963, filed Jun. 21, 2001.

GOVERNMENT SUPPORT

This invention was made in part with government support under grant number CA60499 from the NIH, and US Army Medical Research Post-doctoral Fellowship number: DAMD17-00-1-0166. The government may have certain rights in this invention.

FIELD OF THE INVENTION

The invention relates to use of geminin molecules and Orc3N molecules and the nucleic acids that encode them in the prevention and treatment of viral infections.

BACKGROUND OF THE INVENTION

A wide variety of viral infections exist in humans and the symptoms of infection, time course of infection, and mechanisms of viral replication differ depending on the type of virus. For example, the time course of the primary infection of some viruses, such as influenza and measles, ranges from several days to several weeks, and in contrast, the time course of viruses such as human immunodeficiency virus (HIV), herpesvirus, and papillomavirus, which may be months to years and beyond.

In addition to primary infection, some viruses, for example the herpesviruses, can also cause persistent or latent infections. Herpesviruses persist in a subject by establishing long-term latency in some cells. In the latent state, the viruses do not evoke the normal immune response, but the latency is not absolute, and at times the latent herpesviruses may be reactivated. Herpesviruses are also shed intermittently or continuously at a low level by healthy humans, thereby continuing the potential for viral infection in other individuals. (see Harrison's Principles of Internal Medicine, 14/e, McGraw Hill Companies, New York, 1998).

Epstein-Barr virus (EBV) is an example of a commonly occurring member of the herpesvirus family, which also includes other members such as: herpes simplex virus 1, herpes simplex virus 2, and varicella zoster. Epstein-Barr virus (EBV) is a 165-kb double-stranded DNA virus of the herpesvirus family that replicates as an episome in latently infected cells. B cells or epithelial cells are latently infected by EBV in 90% of humans and can cause lymphoproliferative disease in immunosuppressed subjects and carcinomas. To prevent this problem in patients with AIDS or those who are therapeutically immunosuppressed following transplantation, there is a critical need for strategies to interfere with the EBV infection process.

Acute infection with EBV reportedly is the cause of infectious mononucleosis and is also known to be associated with human tumors including nasopharyngeal carcinoma, Burkitt's lymphoma, Hodgkin's disease, and B cell lymphoma, each of which may arise as a secondary effect of the EBV infection. Additional secondary conditions that may also be associated with EBV infection include autoimmune disorders such as rheumatoid arthritis and Sjögren's syndrome.

The available treatment options for EBV infection include palliative support and symptomatic treatments such as rest and pain relievers. There are no available methods to prevent EBV infection or to eliminate the virus from latently infected cells. Options for reducing the likelihood of contracting a viral infection, such as an EBV infection, and treatments for existing EBV infection are critical to reduce the number of primary and secondary complications of this viral disease.

SUMMARY OF THE INVENTION

We believe that prevention of initial EBV infection will reduce the incidence of EBV-associated illness such as infectious mononucleosis and eliminate potential complications from such diseases. In addition, treatment for primary or latent EBV infection will not only reduce the incidence of infectious mononucleosis, but will also reduce the number of patients who progress to one of the more serious secondary effects of EBV, such as nasopharygeal carcinoma in immunocompetent people and polyclonal and monoclonal lymphoproliferative disorders in immunocompromised people.

In view of the nexus between EBV infection and infectious mononucleosis, various carcinomas, and immunologically based disorders, a need exists for agents that can selectively inhibit EBV replication in human cells. Such agents would be useful as a much-needed prophylactic, and also as a treatment for primary and latent EBV infection. Accordingly, the invention is based, in part, on the discovery that geminin and amino terminal fragments of Orc3, such as Orc3N (alone or in combination with each other), inhibit replication of viruses, such as papillomaviruses, polyomaviruses, and herpesviruses (e.g. EBV, herpes simplex 1, herpes simplex 2, varicella zoster, cytomegalovirus, rhadinovirus, and roseolovirus). The invention provides methods for preventing, inhibiting, and treating viral infection, including EBV infection. Surprisingly, geminin molecules and Orc3N (also known as Orc3N200), which comprises a 200 amino acid N-terminal fragment of human Orc3, each inhibits replication of EBV. Although not wishing to be bound to a particular theory or mechanism, it is believed that geminin and Orc3N each inhibits EBV at the origin of replication (oriP), thereby serving to prevent, inhibit, or treat viral infections. Thus, the invention embraces the use of geminin and Orc3N polypeptides, and the nucleic acids that encode these molecules in the prevention and treatment of viral infections.

According to a first aspect of the invention, methods for treating a viral infection in a subject who is otherwise free of indications for geminin treatment are provided. The methods involve administering to the subject who is otherwise free of indications for geminin treatment a therapeutically effective amount of a geminin molecule to treat the viral infection in the subject. In certain embodiments of the invention, the geminin molecule is a geminin nucleic acid molecule such as the geminin nucleic acid molecule that includes SEQ ID NO: 1 or 9, or the gemininΔDB (also known as geminin ΔD-Box) nucleic acid molecule that includes SEQ ID NO: 3. Additionally, or alternatively, the geminin molecule is a geminin polypeptide, such as those that include SEQ ID NOs: 2, 4, or 10.

According to a second aspect of the invention, methods for treating a viral infection in a subject who is otherwise free of indications for Orc3N treatment are provided. The methods involve administering to the subject who is otherwise free of indications for Orc3N treatment a therapeutically effective amount of an Orc3N molecule to treat the viral infection in the subject. In certain embodiments, the Orc3N molecule is an Orc3N nucleic acid molecule that includes SEQ ID NO: 5 or an Orc3N polypeptide that includes SEQ ID NO: 6

In some embodiments of the foregoing methods, the viral infection is a herpesvirus infection. For example, the herpesvirus is selected from the group consisting of: Epstein Barr Virus (EBV or HHV-4), roseolovirus (e.g. HHV-6, HHV-7), cytomegalovirus, (e.g. HCMV/HHV-5), Simplexvirus (e.g. Herpes Simplex Virus 1, Herpes Simplex Virus 2), rhadinovirus (HHV-8), and varicello virus, (e.g. varicella zoster). In certain embodiments of the foregoing methods, the viral infection is infection by Epstein-Barr virus. For example, the EBV infection is a latent infection of human epithelial cells and/or B cells. In other embodiments of the foregoing methods, the viral infection is a papillomavirus infection. In some embodiments of the foregoing methods, the viral infection is a polyomavirus infection, such as by JC virus or SV40 virus.

In certain embodiments of the foregoing methods, the viral infection is an infection with a virus that replicates as episomes in cells. In some embodiments of the foregoing methods, the virus replicates as episomes in human cells.

In certain embodiments of the foregoing methods, the subject is a human. In some embodiments of the foregoing methods, the subject is immunocompromised and in other embodiments of the foregoing methods, the subject is immunocompetent.

It is noted that the preferred subjects treated according to the first aspect of the invention are otherwise free of symptoms calling for geminin molecule treatment. For example, geminin has been suggested as an agent for treating proliferative disorders (e.g. cancer) and neurological disorders including: Parkinson's disease, Alzheimer's disease, multiple sclerosis, and spinal cord injury (see for example, PCT patent publication number WO99/58673). Accordingly, the preferred subjects for treating this aspect of the invention are free of the foregoing conditions.

It is also noted that the preferred subjects treated according to the second aspect of the invention are otherwise free of symptoms calling for Orc3N molecule treatment. For example, it has been suggested that agents that interfere with binding between members of the ORC family of proteins/polypeptides may be useful to control cell growth, for example in cancer or infection with a nonviral pathogen (see for example: U.S. Pat. No. 5,614,618, U.S. Pat. No. 5,589,341). Accordingly, the preferred subjects for treating this aspect of the invention are free of the foregoing conditions.

In yet another aspect of the invention, methods for making a medicament are provided. The methods include placing a therapeutic agent selected from the group consisting of: the isolated geminin and/or Orc3N nucleic acid molecules (SEQ ID NOs: 1, 3, 5, and 9), the isolated geminin and/or Orc3N polypeptides (SEQ ID NOs: 2, 4, 6, and 10), in a pharmaceutically acceptable carrier. Thus, in a related aspect, the invention provides a method for forming a medicament that involves placing a therapeutically effective amount of the therapeutic agent in the pharmaceutically acceptable carrier to form one or more doses.

According to another aspect of the invention, methods of treatment of a viral infection in a subject free of cancer, Parkinson's disease, Alzheimer's disease, multiple sclerosis, and spinal cord injury are provided. The methods include administering to the subject who is free of cancer, Parkinson's disease, Alzheimer's disease, multiple sclerosis, and spinal cord injury a therapeutically effective amount of a geminin molecule and/or an Orc3N molecule to treat the viral infection in the subject.

The geminin polypeptides of the foregoing embodiments of the invention include fragments/pieces of a geminin molecule. These fragments are shorter than the full-length geminin molecule. The geminin polypeptides of the invention include but are not limited to the polypeptides set forth as SEQ ID NOs:11–17.

These and other aspects of the invention will be described in greater detail below. Throughout this disclosure, all technical and scientific terms have the same meaning as commonly understood by one of ordinary skill in the art to which this invention pertains unless defined otherwise.

All documents and publications referred to in this application are incorporated in their entirety herein by reference.

BRIEF DESCRIPTION OF THE DRAWINGS

The drawings are not required for enablement of the claimed invention.

FIG. 1A shows a schematic drawing WT ORC2 locus with the targeting vector and the resultant mutated locus. Solid boxes represent first 4 exons. FIG. 1B shows the results of a Southern blot of EcoRI- or SphI-digested genomic DNA from targeted and wild type HCT116 cells hybridized with the probes shown in FIG. 1A. The asterisks indicate DNA fragments specific to the mutated (−) allele: a 5 kb EcoRI fragment recognized by the neo probe or the 3' probe and a 4 kb SphI fragment recognized by the 3' probe. FIG. 1C shows Cre-mediated recombination of the −/+cells obtained in FIG. 1B produces a Δ/+cell where the excision of the Neo cassette leaves a loxP site in exon 3 (Δ). The second round of targeting can either create a −/+cell or a Δ/−cell. PCR with indicated primers "a" and "c" produce the diagnostic PCR products shown to the right of each allele. EcoRI digestion of the PCR products yields the fragments in parentheses. FIG. 1D shows an immunoblot of genomic DNA prepared from parental Δ/+clone and from −/+ or Δ/−product clones subjected to PCR with primer pairs "a" and "c" shown in 1C. Gel electrophoresis and ethidium bromide stain were utilized to visualize the products of the PCR reaction (top) or the fragments produced by EcoRI digestion of the PCR products (bottom).

FIG. 2A shows the results of western blot analysis of total cell lysates using anti-Orc2, anti-Orc3 and anti-Orc4 antibodies. 5 μg of lysates of WT (+/+) or Δ/−cells loaded per lane. In FIG. 2B, the indicated amounts of cell lysates were loaded to quantitate the low level of the 68 kD ΔOrc2 protein in the lysates of Δ/−cells. The amount of ΔOrc2 in 100 μg of Δ/−cell lysate is comparable to the amount of Orc2 protein in 5–10 μg of WT cell lysate. FIG. 2C shows detection of various replication proteins in the chromatin fraction of WT and Δ/−cells. 2 and 4 μg of protein from the chromatin fraction immunoblotted with antibodies to indicated proteins. FIG. 2D shows immunoprecipitation of 100 μg of chromatin proteins from WT and Δ/−cells with anti-Orc2 antibody followed by immunoblotting with antibodies to Orc2 and Orc3.

FIG. 3A shows cell proliferation of the indicated cell-lines measured by MTT assay. Doubling times were determined by fitting the data to an exponential curve. FIG. 3B shows FACS analysis for DNA content of +/+(WT) and Δ/−HCT116 cells. Cells synchronized at the G1-S boundary by mimosine (left) and 24 hrs following release from the mimosine block (right). FIG. 3C illustrates $^3$H-thymidine incorporation of +/+ and Δ/−cells. Comparison of thymidine incorporation of asynchronous cells growing over 3 days and 5 days in culture, with the incorporation in +/+cells held at 100%. Mean and standard deviation of 6 measurements. FIG. 3D shows a graph of incorporation of thymidine during 1 hour pulses at indicated time-points following release from mimosine block. The thymidine incorporation at each time-point is normalized to the incorporation of that cell-line in the 0 hr time-point.

FIG. 4A shows a Southern blot to detect DpnI resistant plasmids that have replicated in mammalian cells. In indicated lanes DpnI was used to digest unreplicated DNA retaining the dam methylation acquired in E. coli. Plasmid DNA in all lanes was linearized with BamHI and detected by probing with the entire plasmid. The plasmids were either obtained after transfection of HCT116 cells (+/+ or Δ/−) or from E. coli (Bact). Lane 1. Stable replication of p220.2 in hygromycin resistant colonies derived from WT HCT116 cells 10 days after transfection. Lanes 6–7. Transient replication of p367 96 hr following transfection of indicated cell lines. Lanes 2–5. Plasmid obtained directly from bacteria, mixed with cellular genomic DNA from mock transfected cells and digested with indicated enzymes to provide size markers for DpnI resistant plasmid (lanes 3 and 4) and control for complete DpnI digestion (lanes 2 and 5). FIG. 4B shows an immmunoblot of Δ/−HCT116 cells (left) and same cells 48 hr following infection with adenovirus expressing Orc2. 10 μg total cell lysate immunoblotted with anti-Orc2 antibody. * indicates a background band indicating equal loading in the two lanes. FIG. 4C shows p367 replication in Δ/−HCT116 infected with adenovirus expressing GFP (G, lane 3) or Orc2 (O2, lane 4). Lane 1 and 2 contain bacterial p367 mixed with genomic DNA from mock transfected Δ/−HCT116 cells. DNA in all lanes was linearized with BamHI, and in indicated lanes digested with DpnI.

FIG. 6A shows purified ORC1, 2, 3, 4, 6 and GSTORC5 proteins and crude lysate (input) immunoblots using ORC1-6 antibodies. FIG. 6 shows immunoblots of baculovirus-expressed ORC2-5 and GST as control. Cell lysate was purified on GST beads and immunoblotted. FIG. 6C shows immunoblots from baculovirus-expressed ORC2, 3, 4 and GST-ORC5 with proteins purified on GST beads fractionated on a Superose 12 gel filtration column. Alternate fractions were immunoblotted using anti-ORC2, 3, 4 and anti-GST antibodies. The positions of the molecular mass markers thyroglobulin (670 kDa), bovine gamma globulin (158 kDa), chicken ovalbumin (44 kDa), are shown on top. Input lanes were loaded with 5% of the total lysate passed through the column.

FIG. 9A shows full-length ORC3 or different N-terminal deletions of ORC3 and their ability to bind either GST or GSTORC2 in a pull-down experiment on glutathione agarose beads coated with GST, GSTORC2 (GSTO2). The labeled proteins were visualized by SDS-PAGE followed by fluorography. FIG. 9B shows GST pull down experiment using GSTORC2C (C-terminal portion of ORC2) and in vitro transcribed and translated full-length ORC3 (1) or ORC3N200 (3). FIG. 9C shows full-length ORC3 or different C-terminal deletions of ORC3.

FIG. 11A shows baculovirus-expressed GSTORC5, 2, 4 and ORC3N200 proteins bound to glutathione agarose beads immunoblotted using either anti-GST or anti-ORC antibodies. FIG. 11B shows immunoprecipitation using anti-ORC2 and anti-ORC3 antibodies. Cell lysate from FIG. 11A was immunoprecipitated using either anti-ORC2 or anti-ORC3 antibodies followed by immunoblotting with either anti-ORC3 or anti-ORC2 antibodies. In each case 5% of the lysate (used for immunoprecipitation) was loaded in the input lanes.

BRIEF DESCRIPTION OF THE SEQUENCES

Figure 1:
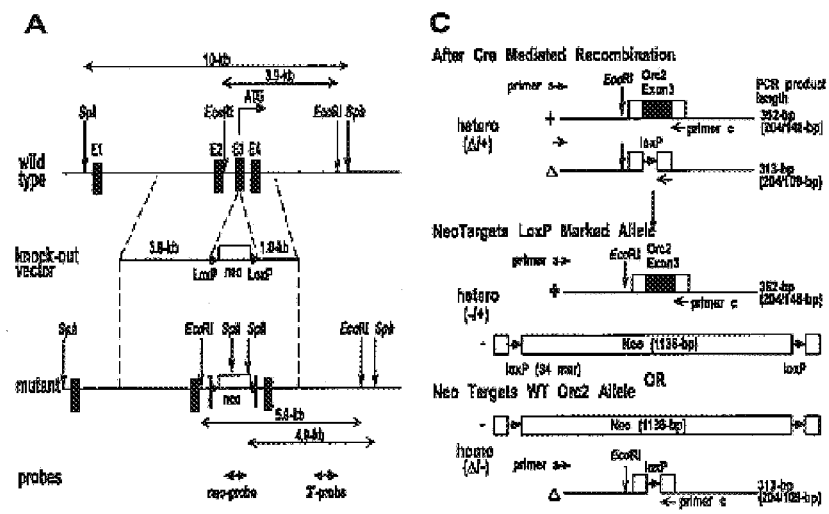
FIG. 1 demonstrates targeted disruption of the human ORC2 gene.
Figure 1:
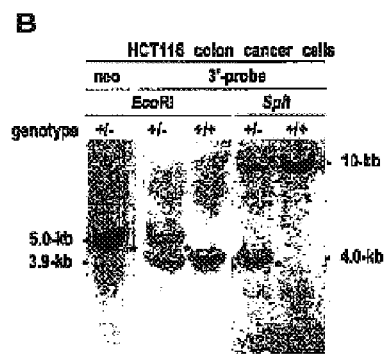
Figure 1:
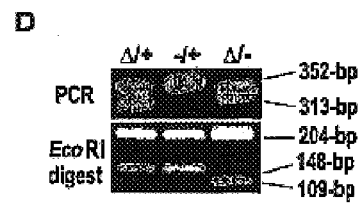

SEQ ID NO: 1 is geminin nucleic acid ORF sequence (from GenBank No: XM_004261).

SEQ ID NO: 2 is geminin amino acid sequence (GenBank No: XP_004261).

SEQ ID NO:3 is gemininΔD (geminin ΔD-box) nucleic acid.

SEQ ID NO:4 is gemininΔD (geminin ΔD-Box) amino acid sequence.

SEQ ID NO:5 is Orc3N (Orc3N200) nucleic acid sequence.

SEQ ID NO:6 is Orc3N (Orc3N200) amino acid sequence.

SEQ ID NO:7 is 5'-agctaccttgattggatttagctc-3'.

SEQ ID NO:8 is 5'-acctccttctctatctagaatgtg-3'.

SEQ ID NO:9 is geminin fragment (aa70–152) nucleic acid sequence.

SEQ ID NO:10 is geminin fragment (aa70–152) amino acid sequence.

SEQ ID NO:11 is PESSENKNLGGVTQESFDLMIKEN

SEQ ID NO:12 is PESSENKNLGGVTQESFDLMIKENPSSQY

SEQ ID NO:13 is PESSENKNLGGVTQESFDLMIKENPSSQYWKE

SEQ ID NO:14 is PGVIVPESSENKNLGGVTQESFDLMIKEN

SEQ ID NO:15 is LTSTTSSPGVIVPESSENKNLGGVTQESFDLMIKEN

SEQ ID NO: 16 is PGVIVPESSENKNLGGVTQESFDLMIKENPSSQY

SEQ ID NO:17 is LTSTTSSPGVIVPESSENKNLGGVTQESFDLMIKENPSSQY

DETAILED DESCRIPTION OF THE INVENTION

The invention is based, in part, on the discovery that geminin and Orc3N (alone or in combination) inhibit replication of viruses, such as herpesviruses [e.g. EBV HHV-4, herpes simplex 1, herpes simplex 2, cytomegalovirus, roseolovirus (HHV-6, HHV-7), rhadinovirus (HHV-8), and varicello virus (varicella zoster)], papillomaviruses, and polyomaviruses (e.g. JC virus and SV40 virus). Geminin molecules and Orc3N, which comprises a 200 amino acid, N-terminal fragment of human Orc3, each inhibits replication of EBV. Although not wishing to be bound to a particular theory or mechanism, it is believed that geminin and Orc3N each inhibits EBV at the origin of replication, (oriP), and geminin polypeptides and/or Orc3N polypeptides can be administered to prevent or treat viral infections in a subject. Geminin and Orc3N can also be tested in screening assays to assess their effectiveness as inhibitors of other viruses, including but not limited to: retroviruses, hepatitis B virus, and other viruses that replicate as episomes. Although not wishing to be bound to a particular theory, it is believed that geminin and Orc3N inhibit viral replication in viruses that replicate as episomes in cells, for example, human cells. Based on the screening results, compositions for treatment of the viruses with geminin and/or Orc3N molecules may be prepared and administered according to methods described herein.

Geminin Compositions and Utilities

According to a first aspect of the invention, methods for treating a viral infection in a subject who is otherwise free of indications for geminin treatment are provided. The methods involve administering to the subject who is otherwise free of indications for geminin treatment a therapeutically effective amount of a geminin molecule to treat the viral infection in the subject. In certain embodiments of the invention, the geminin molecule is a geminin nucleic acid molecule such as the geminin nucleic molecule having SEQ ID NO: 1 or 9 or the gemininΔDB molecule having SEQ ID NO: 3 Additionally or alternatively, the geminin molecule is a geminin polypeptide, such as those having SEQ ID NO: 2, 4, or 10.

A subject, as used herein in the first aspect of the invention, refers to any mammal (preferably, a human) that may be susceptible to, or have, a viral infection, for example, EBV infection, provided that the mammal is otherwise free of symptoms calling for geminin treatment. Exemplary conditions that have been suggested for treatment with geminin include: proliferative disorders, e.g. cancer, neurological disorders including: Parkinson's disease, Alzheimer's disease, multiple sclerosis, and spinal cord injury.

A "geminin molecule", as used herein, embraces both "geminin nucleic acids" and "geminin polypeptides." Geminin molecules are capable of inhibiting viral replication. Accordingly, geminin molecules are capable of reducing or preventing the acute or latent viral infections in vivo and in vitro by inhibiting viral replication in infected cells and cells exposed to the viral pathogen.

The invention embraces the use of geminin polypeptides, and functional equivalents thereof, and the nucleic acids that encode these molecules in the prevention and treatment of viral infections. PCT patent publication number WO 99/58673, the entire contents of which are incorporated by reference herein, suggests the use of geminin and functional equivalents of geminin (see pages 14–17) for treating the above-noted non-viral disorders and also describes the nucleic acids that encode geminin and fragments thereof (see pages 17–20). In addition WO 99/58673 teaches methods for administration of geminin, (see pages 20–23) which are applicable in the present invention.

The geminin nucleic acid molecules, preferably isolated, that are useful for practicing the invention, are selected from the group consisting of:

(a) nucleic acid molecules which hybridize under stringent conditions to a nucleic acid molecule having a nucleotide sequence set forth as SEQ ID NO:1 or SEQ ID NO:3 or SEQ ID NO:9, and which code for a geminin polypeptide, (b) deletions, additions and substitutions of the nucleic acid molecules of (a), and which code for a geminin polypeptide, (c) nucleic acid molecules that differ from the nucleic acid molecules of (a) or (b) in codon sequence due to the degeneracy of the genetic code, and (d) complements of (a), (b), or (c).

The preferred isolated nucleic acids of a first aspect of the invention are geminin nucleic acid molecules which encode a geminin polypeptide having SEQ ID NO: 2, 4, or 10. In the preferred embodiments of the first aspect of the invention, the isolated nucleic acid molecule is SEQ ID NO:1 or SEQ ID NO:3 or SEQ ID NO:9.

The geminin polypeptides, preferably isolated, that are useful for practicing the invention are encoded by the above-described geminin nucleic acid molecules. Thus, geminin polypeptides embrace polypeptides having SEQ ID NOs: 2, 4, and 10, as well as geminin polypeptide fragments, and polypeptides with amino acid sequences analogous to the amino acid sequences of the geminin polypeptide and functional equivalents thereof. Such polypeptides are defined herein as geminin analogs, homologs, derivatives, or fragments. As used herein, the term "geminin polypeptide" is meant to include the geminin polypeptide and functional equivalents thereof. Thus, a geminin polypeptide refers to a polypeptide that is encoded by a nucleic acid including SEQ ID NO:1, 3, or 9, or a functional fragment thereof, or a functional equivalent thereof (e.g., a nucleic acid sequence encoding the same polypeptide as encoded by SEQ ID NO:1, 3, or 9), provided that the functional fragment or equivalent encodes a polypeptide that exhibits a geminin functional activity. As used herein, a geminin functional activity refers to the ability of a geminin molecule to modulate replication of viruses, such as EBV. An exemplary geminin functional activity is a viral replication suppressor activity such as inhibiting (also referred to as suppressing and/or reducing) viral cell replication. Although not wishing to be bound to any particular theory or mechanism, it is believed that the geminin polypeptide may affect at least some of the above-noted cell functions by interacting with the replication initiator complex at ori(P), thereby, inhibiting viral replication.

The geminin polypeptides of the invention include fragments/pieces of a geminin molecule. These fragments are shorter than the full-length geminin molecule.

The geminin polypeptides and geminin fragments of the invention can be screened for inhibition of viral replication using the same type of assays as described herein (e.g. in the Examples section). Using such assays, the geminin polypeptides that have the best inhibitory activity can be identified. It is understood that any mechanism of action described herein for the geminin polypeptides is not intended to be limiting, and the scope of the invention is not bound by any such mechanistic descriptions provided herein.

The geminin polypeptides of the invention include sequences that contain PESSENKNLGGVTQESFDLMIKEN (SEQ ID NO:11) and 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, or 116 additional amino acids at its C-terminal end, wherein the amino acids that are added are identical to the corresponding amino acid in that position in the full-length human geminin amino acid sequence (Genbank accession number XP_004261, SEQ ID NO:2). For example, the human geminin polypeptide that has five additional amino acids at the C-terminal end will have the amino acid sequence: PESSENKNLGGVTQESFDLMIKENPSSQY (SEQ ID NO:12), and the geminin polypeptide that has eight additional amino acids at the C-terminal end will have the amino acid sequence: PESSENKNLGGVTQESFDLMIKENPSSQYWKE (SEQ ID NO:13).

The geminin polypeptides of the invention also include sequences that includes PESSENKNLGGVTQESFDLMIKEN (SEQ ID NO:11) and has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 additional amino acids at its N-terminal end, wherein the amino acids that are added are identical to the corresponding amino acid in that position in the full-length human geminin sequence (Genbank Accession number XP004261, SEQ ID NO:2). For example, the geminin polypeptide that has five additional amino acids at the N-terminal end will have the amino acid sequence: PGVIVPESSENKNLGGVTQESFDLMIKEN (SEQ ID NO:14), and the geminin polypeptide that has twelve additional amino acids at the N-terminal end will have the amino acid sequence: LTSTTSSPGVIVPESSENKNLGGVTQESFDLMIKEN (SEQ ID NO:15).

The geminin polypeptides of the invention also include sequences that includes PESSENKNLGGVTQESFDLMIKEN (SEQ ID NO:11) and has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, or 116 additional amino acids at its C-terminal end and has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, or 69 additional amino acids at its N-terminal end, wherein the amino acids that are added will be identical to the amino acid in that position in the full-length human geminin sequence (Genbank Accession number XP_04261, SEQ ID NO:2). For example, the geminin polypeptide that has five additional amino acids at the N-terminal end and five additional amino acids at its C-terminal end will have the amino acid sequence: PGVIVPESSENKNLGGVTQESFDLMIKENPSSQY (SEQ ID NO:16), and the human polypeptide that has 12 additional amino acids at the N-terminal end and five additional amino acids at its C-terminal end, will have the amino acid sequence: LTSTTSSPGVIVPESSENKNLGGVTQESFDLMIKENPSSQY (SEQ ID NO: 17). The geminin polypeptides of the invention also include sequences that are smaller than PESSENKNLGGVTQESFDLMIKEN (SEQ ID NO:11) and it will be understood that the sequence can be reduced in size by 1, 2, 3, 4, 5, 6, 7, 8, 9, 10, 11, 12, or 13 amino acids from either or both termini, provided that the remaining sequence is at least about 10 amino acids in length.

The geminin nucleic acids of the invention are those nucleic acids that encode the geminin polypeptides of the invention as described herein. The amino acid sequences identified herein as geminin polypeptides, and the nucleotide sequences encoding them, are sequences deposited in databases such as GenBank.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid molecule as used herein is not a naturally occurring chromosome.

The polypeptides useful for practicing the invention can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, also can be synthesized chemically using well-established methods of peptide synthesis.

Thus, as used herein with respect to polypeptides, "isolated" means separated from its native environment and present in sufficient quantity to permit its identification or use. Isolated, when referring to a polypeptide, means, for example: (i) selectively produced by expression of a recombinant nucleic acid or (ii) purified as by chromatography or electrophoresis.

Isolated polypeptides may, but need not be, substantially pure. The term "substantially pure" means that the polypeptides are essentially free of other substances with which they may be found in nature or in in vivo systems to an extent practical and appropriate for their intended use. Substantially pure polypeptides may be produced by techniques well known in the art. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, i.e. isolated from other polypeptides.

Homologs and alleles of the geminin polypeptides of the invention can be identified by conventional techniques. As used herein, a homolog to a geminin polypeptide is a polypeptide from a human or other animal that has a high degree of structural similarity to the identified geminin polypeptide, e.g., at least 95% amino acid sequence identity.

Identification of human and other organism homologs of geminin polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode geminin polypeptides identified herein to screen the library for related nucleotide sequences. The screening preferably is performed using high-stringency conditions to identify those sequences that are closely related by sequence identity. Nucleic acids so identified can be translated into polypeptides and the polypeptides can be tested for a geminin functional activity, (e.g. a viral-inhibition activity).

The term "high stringency" as used herein refers to parameters with which the art is familiar. Nucleic acid hybridization parameters may be found in references that compile such methods, e.g. *Molecular Cloning: A Laboratory Manual,* J. Sambrook, et al., eds., Second Edition, Cold Spring Harbor Laboratory Press, Cold Spring Harbor, N.Y., 1989, or *Current Protocols in Molecular Biology,* F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of geminin polypeptide nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecules and sequencing.

In general, geminin homologs and alleles typically will share at least 90% nucleotide identity and/or at least 95% amino acid identity to the sequences of geminin polypeptides or fragments thereof, and precursors thereof. Nucleic acid and polypeptides, respectively, in some instances will share at least 95% nucleotide identity and/or at least 97% amino acid identity, and in other instances will share at least 97% nucleotide identity and/or at least 99% amino acid identity. The percent identity can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for geminin polypeptide genes, a Southern blot may be performed using the foregoing conditions, together with a detectably labeled probe (e.g. radioactive or chemiluminescent probes). After washing the membrane to which the DNA is finally transferred, the membrane can be placed against X-ray film or a phosphorimager to detect the radioactive or chemiluminescent signal. In screening for the expression of geminin polypeptide nucleic acids, Northern blot hybridizations using the foregoing conditions can be performed on samples taken from viral-infected subjects (for example subjects with EBV) or subjects suspected of having a condition characterized by viral infection (e.g. EBV infection). Amplification protocols such as polymerase chain reaction using primers that hybridize to the sequences presented also can be used for detection of the geminin polypeptide genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library.

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating geminin polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1–20 nucleotides that are useful for practicing the invention). In preferred embodiments, these modified nucleic acid molecules and/or the polypeptides they encode retain at least one activity or function of the unmodified nucleic acid molecule and/or the polypeptides, such as viral inhibition, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under high stringency conditions known to one of skill in the art.

For example, modified nucleic acid molecules that encode polypeptides having single amino acid changes can be prepared. Each of these nucleic acid molecules can have one, two, or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

Fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Fragments also can be used to produce fusion proteins for generating antibodies or determining binding of the polypeptide fragments, or for generating immunoassay components. Likewise, fragments can be employed to produce nonfused fragments of the geminin polypeptide, useful, for example, in the preparation of antibodies, and in immunoassays. The antibodies can be used, for example, to identify specific epitopes in geminin that are responsible for viral modulation. Preferred fragments are fragments that inhibit viral replication.

Fragments of a polypeptide preferably are those fragments that retain a distinct functional capability of the polypeptide. Functional capabilities that can be retained in a fragment of a polypeptide include the ability to inhibit viral replication. As will be recognized by those skilled in the art, the size of the fragment will depend upon factors such as whether the fragment is of sufficient size to inhibit viral replication. Thus, some fragments of geminin polypeptides will consist of longer segments while others will consist of shorter segments, (e.g. 5, 6, 7, 8, 9, 10, 11 or 12 or more amino acids long, including each integer up to the full length of the geminin polypeptide). Those skilled in the art are well versed in methods for selecting functional fragments of polypeptides.

The skilled artisan will also realize that conservative amino acid substitutions may be made in geminin polypeptides to provide functionally equivalent variants, or homologs of the foregoing polypeptides, i.e, the variants retain the functional capabilities of the geminin polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual,* J. Sambrook, et al., eds., Second Edition, Cold Spring Harbor Laboratory Press, Cold Spring Harbor, N.Y., 1989, or *Current Protocols in Molecular Biology,* F. M. Ausubel, et al., eds., John Wiley & Sons, Inc., New York. Exemplary functionally equivalent variants or homologs of the geminin polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. For example, upon determining that a peptide is a geminin-equivalent polypeptide, one can make conservative amino acid substitutions to the amino acid sequence of the peptide, and still have the polypeptide retain its specific viral replication inhibition characteristics.

Conservative amino-acid substitutions in the amino acid sequence of geminin polypeptides to produce functionally equivalent variants of geminin polypeptides typically are made by alteration of a nucleic acid encoding geminin polypeptides. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a geminin polypeptide. Where amino acid substitutions are made to a small unique fragment of a geminin polypeptide, the substitutions can be made by directly synthesizing the peptide. The activity of functionally equivalent fragments of geminin polypeptides can be tested by cloning the gene encoding the altered geminin polypeptide into a bacterial or mammalian expression vector, introducing the vector into an appropriate host cell, expressing the altered polypeptide, and testing for a functional capability of the geminin polypeptides as disclosed herein. Peptides that are chemically synthesized can be tested directly for function, e.g., for inhibiting viral (e.g. EBV) replication.

Compositions of the various forms of the geminin nucleic acid molecules and polypeptides useful for practicing the invention are described herein. In general these compositions are prepared in the manner described in PCT publication number WO99/58673, the contents of which is in its entirety hereby incorporated by reference. To accomplish the various treatments as described herein, a nucleic acid that encodes geminin or a functional portion or domain thereof is introduced into a mammalian cell (e.g., mammalian somatic cell, mammalian germ line cell (sperm and egg cells)). This can be accomplished by inserting the isolated nucleic acid that encodes either the full length geminin polypeptide, the C-terminal domain, the N-terminal domain, or the domains described herein, or a functional equivalent thereof, into a nucleic acid vector, e.g., a DNA vector such as a plasmid, virus or other suitable replicon (e.g., a viral vector), which can be present in a single copy or multiple copies. The nucleic acid can be transfected or transformed into cells using suitable methods known in the art such as electroporation, microinjection, infection, and lipofection and direct uptake. Such methods are described in more detail, for example, in Sambrook et al., "Molecular Cloning: A Laboratory Manual," 2nd ED. (1989), Ausubel, F. M., et al., Current Protocols in Molecular Biology, (Current Protocol, 1994) and Sambrook et al., "Molecular Cloning: A Laboratory Manual," 2nd, ED. (1989).

Geminin can be used to prevent and/or treat a viral infection by delivering to cells the geminin molecules, described herein, in vitro or in vivo. The cells to which geminin molecules may be delivered in vitro include, but are not limited to, cultured cells. Examples of cultured cells to which geminin may be delivered to prevent and/or treat a viral infection, include but are not limited to, cells used to produce recombinant proteins and cells to be transplanted into a subject (e.g. bone marrow, blood cells, kidney cells, corneal cells, liver cells and stem cells).

Geminin molecules can be delivered to a cell in vitro or in vivo by the use of viral vectors comprising one or more nucleic acid sequences encoding a geminin polypeptide. Generally, the nucleic acid sequence has been incorporated into the genome of the viral vector. The viral vector containing nucleic acid sequences encoding the geminin polypeptide can be contacted with a cell in vitro or in vivo and infection can occur. The cell can then be used experimentally to study, for example, the effect of geminin molecules on viral replication in vitro or the cells can be implanted into a subject for therapeutic use. The cell can be migratory, such as hematopoietic cells, or non-migratory. The cell can be present in a biological sample obtained from the subject (e.g., blood, bone marrow) and used in the treatment of disease, or can be obtained from cell culture and used to dissect viral replication pathways in in vivo and in vitro systems.

After contact with the geminin polypeptide or with the viral vector comprising a nucleic acid sequence encoding geminin, the subject sample can be returned to the subject or re-administered to a culture of subject cells according to methods known to those practiced in the art. In the case of delivery to a subject or experimental animal model (e.g., rat, mouse, monkey, chimpanzee), such a treatment procedure is sometimes referred to as ex vivo treatment or therapy. Frequently, the cell is taken from the subject or animal and returned to the subject or animal once contacted with the viral vector comprising the nucleic acids of the present invention. Ex vivo gene therapy has been described, for example, in Kasid, et al., Proc. Natl. Acad. Sci. USA 87:473 (1990); Rosenberg, et al., New Engl. J Med. 323:570 (1990); Williams, et al., Nature 310476 (1984); Dick, et al., Cell 42:71 (1985); Keller, et al, Nature 318:149 (1985) and Anderson, et al., U.S. Pat. No. 5,399,346 (1994).

Where a cell is contacted in vitro, the cell incorporating the viral vector comprising a nucleic acid sequence of geminin can be implanted into a subject or experimental animal model for delivery or used in in vitro experimentation to study cellular events mediated by geminin.

Various viral vectors can be used to introduce the geminin nucleic acid into mammalian cells. Viral vectors include retrovirus, adenovirus, parvovirus (e.g., adeno-associated viruses), coronavirus, negative-strand RNA viruses such as orthomyxovirus (e.g., influenza virus), rhabdovirus (e.g., rabies and vesicular stomatitis virus), paramyxovirus (e.g. measles and Sendai), positive-strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g. vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

A preferred method to introduce nucleic acid that encodes geminin into cells is through the use of engineered viral vectors. These vectors provide a means to introduce nucleic acids into cycling and quiescent cells, and have been modified to reduce cytotoxicity and to improve genetic stability. The preparation and use of engineered Herpes simplex virus type 1 (D. M. Krisky, et al., Gene Therapy 4(10):1120–1125. (1997)), adenoviral (A. Amalfitanl, et al., Journal of Virology 72(2):926–933. (1998)), attenuated lentiviral (R. Zufferey, et al., Nature Biotechnology 15(9)871–875 (1997)) and adenoviral/retroviral chimeric (M. Feng, et al., Nature Biotechnology 15(9):866–870 (1997)) vectors are known to the skilled artisan. In addition to delivery through the use of vectors, geminin nucleic acids may be delivered to cells without vectors, e.g. as "naked" nucleic acid delivery using methods known to those of skill in the art.

Various forms of the geminin polypeptide or nucleic acid, as described herein, can be administered and delivered to a mammalian cell (e.g., by virus or liposomes, or by any other suitable methods known in the art or later developed). The method of delivery can be modified to target certain cells, and in particular, cell surface receptor molecules or antigens present on tumor cells. Methods of targeting cells to deliver nucleic acid constructs are known in the art. The geminin polypeptide can also be delivered into cells by expressing a recombinant protein fused with peptide carrier molecules, examples of which, though not intended to be limiting, are tat or antennapedia. These delivery methods are known to those of skill in the art and are described in U.S. Pat. No. 6,080,724, and U.S. Pat. No. 5,783,662, the entire contents of which are hereby incorporated by reference.

In addition to the methods described herein for delivering exogenous geminin, expression of endogenous geminin can be induced (e.g. upregulated) in cells harboring the virus by the administration of chemicals or other molecules that specifically increase the level of geminin mRNA and/or protein expression. Such induction and/or upregulation of endogenous geminin may occur through methods that include, but not limited to: (a) activation of the geminin promoter, (b) stabilization of geminin mRNA, (c) increased translation of geminin polypeptide and (d) stabilization of geminin polypeptide.

A geminin polypeptide may be administered using other methods known in the art. For example, the mode of administration is preferable at the location of the target cells. As such, the administration can be intranasal (as in administering a vector expressing a geminin nucleic acid molecule). Other modes of administration (parenteral, mucosal, systemic, implant, intraperitoneal, etc.) are generally known in the art. The agents are preferably administered in a pharmaceutically acceptable carrier, such as saline, sterile water, Ringer's solution, and isotonic sodium chloride solution.

Additional agents, for example small chemicals, that mimic the action of geminin to inhibit viral replication may be identified by selecting an agent that inhibits a target molecule that is a nucleic acid or an encoded protein selected from the group consisting of Orc1, Orc2, Orc3, Orc4, Orc5, Orc6, and a binding partner thereof (e.g., CDC6, Cdt1, MCM protein) (e.g., an agent which selectively binds to any of the foregoing target molecule nucleic acids or proteins and inhibits its transcription/translation/functional activity); and contacting the selected agent with a cell under conditions wherein the cell undergoes viral replication in the absence of an inhibitor, wherein a selected agent which inhibits viral replication is a viral replication inhibitor. Agents that can be tested in this manner include library molecules, such as those describe in U.S. Pat. Nos.: 6,103,869 and 5,663,299.

Administration of Geminin and/or Orc3N

When used therapeutically, the geminin and/or Orc3N molecules of the invention are administered in therapeutically effective amounts. The Orc3N molecules will be described in detail below. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the viral disease in the subject, all of which can be determined by one of ordinary skill in the art.

As used herein, the term "subject is immunocompromised" has its standard meaning as known to one of ordinary skill in the art, and means that the subject has a primary immunodeficiency (genetically determined) and/or a secondary immunodeficiency (acquired) (see: Robbins Pathologic Basis of Disease, $6^{th}$ ed. R. S. Cotran, V. Kumar, and T. Collins. W. B. Saunders Company, Philadelphia, p. 231). As used herein, the term "subject is immunocompetent" has its standard meaning as known to one of skill in the art, and means that the subject does not have an immunodeficiency.

The geminin and/or Orc3N dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

The therapeutically effective amount of the geminin and/or Orc3N molecule is that amount effective to inhibit viral replication, for example EBV replication can be determined using standard tests known in the art. For example, serologic testing can be performed to determine the viral titer in a subject. For example, an EBV-specific antibody testing is used to test subjects suspected of having an acute EBV infection, levels of IgA antibodies to EBV antigens can be determined, determination of levels of IgM and IgG antibody to viral capsid antigen (VC) can be performed to determine the presence of EBV infection. In addition, the heterophile antibody test may be used to diagnose infectious mononucleosis. These types of tests, as well as others known to those of ordinary skill in the medical arts, may be used to assess the viral infection status of a subject and to evaluate a therapeutically effective amount of geminin and/or Orc3N administered. Diagnostic tests for other viruses, including herpesviruses, papillomaviruses, and polyomaviruses are known to those of ordinary skill in the art. (for examples: see Harrison's Principles of Internal Medicine, 14/e, McGraw Hill companies, New York, 1998). A first determination of viral infection may be obtained using one of the methods described above, and a subsequent determination of viral infection can be done and a comparison of the viral infection levels may be used to assess the effectiveness of geminin and/or Orc3N molecule administration as a prophylactic or a treatment of the viral infection. Absence of a viral infection may be an indication for prophylactic intervention by administering geminin polypeptides and/or Orc3N polypeptides to prevent viral (e.g. EBV) infection.

The geminin and/or Orc3N molecules may be administered alone, in combination with each other, and/or in combination with other antiviral drug therapies. Antiviral agents that may be administered with geminin and/or Orc3N may include, but are not limited to: nucleoside analogs, nornnucleoside reverse transcriptase inhibitors, protease inhibitors, integrase inhibitors, including the following: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate, Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Indinavir; Kethoxal; Lamivudine; Lobucavir; Memotine Hydrochloride; Methisazone; Nelfinavir; Nevirapine; Penciclovir; Pirodavir; Ribavirin; Rimantadine Hydrochloride; Ritonavir; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime and integrase inhibitors.

The above-described drug therapies are well known to those of ordinary skill in the art and are administered by modes known to those of skill in the art. The drug therapies are administered in amounts that are effective to achieve the physiological goals (to reduce viral infection, and/or reduce viral titer in a subject), in combination with the geminin and/or Orc3N of the invention. Thus, it is contemplated that the drug therapies may be administered in amounts which are not capable of preventing or reducing the physiological consequences of the viral infections when the drug therapies are administered alone, but which are capable of preventing or reducing the physiological consequences of viral infection when administered in combination with the geminin and/or Orc3N molecules of the invention.

When administered, the geminin polypeptides and/or Orc3N polypeptides of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The therapeutics of the invention can be administered by any conventional route, including injection or by gradual infusion over time. The administration may, for example, be oral, intranasal, intravenous, intraperitoneal, intramuscular, intracavity, subcutaneous, or transdermal. An additional route of administration may be by pulmonary aerosol Techniques for preparing aerosol delivery systems are well known to those of skill in the art. Generally, such systems should utilize components which will not significantly impair the biological properties of the medicament molecules, such as the viral replication inhibition function (see for example, "Aerosols," in *Remington's Pharmaceutical Sciences,* 18th edition, 1990). Those of skill in the art can readily determine the various parameters and conditions for producing aerosols without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The pharmaceutical compositions contain any of the foregoing therapeutic agents in a pharmaceutically acceptable carrier. Thus, in a related aspect, the invention provides a method for forming a medicament that involves placing a therapeutically effective amount of the therapeutic agent in the pharmaceutically acceptable carrier to form one or more doses.

The preparations of the invention are administered in effective amounts. An effective amount, as described above, is that amount of a pharmaceutical preparation that alone, or together with further doses, stimulates the desired response. In the case of treating or preventing viral infection, the desired response is inhibiting the replication and progression of the viral infection. This may involve only slowing the progression of the disease temporarily, although more preferably, it involves halting the progression of the disease permanently. These responses can be monitored by routine methods or can be monitored according to diagnostic methods of the invention discussed herein.

Orc3N Compositions and Utilities

According to a second aspect of the invention, methods for treating a viral infection in a subject who is otherwise free of indications for Orc3N treatment are provided. The methods involve administering to the subject who is otherwise free of indications for Orc3N treatment a therapeutically effective amount of an Orc3N molecule to treat the viral infection in the subject. In certain embodiments of the invention, the Orc3N molecule is an Orc3N nucleic acid molecule having SEQ ID NO: 5 or an Orc3N polypeptide having SEQ ID NO:6.

A subject, as used herein in this aspect of the invention, refers to any mammal (preferably, a human) that may be susceptible to, or have, a viral infection, for example, EBV infection, provided that the mammal is otherwise free of symptoms calling for Orc3N treatment. Exemplary conditions that have been suggested for treatment with Orc3N include: cancer and infection with nonviral pathogens.

An "Orc3N molecule", as used herein, embraces both "Orc3N nucleic acids" and "Orc3N polypeptides". Orc3N molecules are capable of inhibiting viral replication. Accordingly, Orc3N molecules are capable of reducing or preventing the acute or latent viral infections in vivo and in vitro by inhibiting viral replication in infected cells and cells exposed to the viral pathogen.

The invention embraces the use of Orc3N, polypeptides, and functional equivalents thereof, and the nucleic acids that encode these molecules in the prevention and treatment of viral infections. U.S. Pat. Nos. 5,614,618 and 5,589,341, the entire contents of which are incorporated by reference herein, disclose sequences and methods of determining binding of various ORC components (see U.S. Pat. No. 5,614,618 columns 2–5 and U.S. Pat. No. 5,589,341 columns 2–5).

The Orc3N nucleic acid molecules, preferably isolated, that are useful for practicing the invention, are selected from the group consisting of:

(a) nucleic acid molecules which hybridize under stringent conditions to a nucleic acid molecule having a nucleotide sequence set forth as SEQ ID NO:5, and which code for an Orc3N polypeptide, (b) deletions, additions and substitutions of the nucleic acid molecules of (a), and which code for an Orc3N polypeptide, (c) nucleic acid molecules that differ from the nucleic acid molecules of (a) or (b) in codon sequence due to the degeneracy of the genetic code, and (d) complements of (a), (b), or (c).

The preferred isolated nucleic acids of this aspect of the invention are Orc3N nucleic acid molecules which encode an Orc3N polypeptide including SEQ ID. NO:6. In the preferred embodiments of the first aspect of the invention, the isolated nucleic acid molecule is SEQ ID NO:5.

The Orc3N polypeptides, preferably isolated, that are useful for practicing the invention are encoded by the above-described Orc3N nucleic acid molecules. Thus, Orc3N polypeptides embrace polypeptides including SEQ ID NO:6, as well as Orc3N polypeptide fragments, and polypeptides with amino acid sequences analogous to the amino acid sequences of the Orc3N polypeptide and functional equivalents thereof. Such polypeptides are defined herein as Orc3N analogs, homologs, derivatives, or fragments. As used herein, the term "Orc3N polypeptide" is meant to include the Orc3N polypeptide and functional equivalents thereof. Thus, an Orc3N polypeptide refers to a polypeptide that is encoded by a nucleic acid including SEQ ID NO:5, or a functional fragment thereof, or a functional equivalent thereof (e.g., a nucleic acid sequence encoding the same polypeptide as encoded by SEQ ID NO:5), provided that the functional fragment or equivalent encodes a polypeptide that exhibits an Orc3N functional activity. As used herein, an Orc3N functional activity refers to the ability of an Orc3N molecule to modulate replication of viruses, such as EBV. An exemplary Orc3N functional activity is a viral replication suppressor activity such as inhibiting (also referred to as suppressing and/or reducing) viral cell replication. Although not wishing to be bound to any particular theory or mechanism, it is believed that the Orc3N polypeptide may affect at least some of the above-noted cell functions by interacting with the ORC complex at ori(P), thereby, inhibiting viral replication.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid molecule as used herein is not a naturally occurring chromosome.

The polypeptides useful for practicing the invention can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, also can be synthesized chemically using well-established methods of peptide synthesis. Thus, as used herein with respect to polypeptides, "isolated" means separated from its native environment and present in sufficient quantity to permit its identification or use. Isolated, when referring to a polypeptide, means, for example: (i) selectively produced by expression of a recombinant nucleic acid or (ii) purified as by chromatography or electrophoresis. Isolated polypeptides may, but need not be, substantially pure. The term "substantially pure" means that the proteins or polypeptides are essentially free of other substances with which they may be found in nature or in in vivo systems to an extent practical and appropriate for their intended use. Substantially pure polypeptides may be produced by techniques well known in the art. Because an isolated polypeptide may be admixed with a pharmaceutically acceptable carrier in a pharmaceutical preparation, the polypeptide may comprise only a small percentage by weight of the preparation. The polypeptide is nonetheless isolated in that it has been separated from the substances with which it may be associated in living systems, i.e. isolated from other proteins. Homologs and alleles of the Orc3N nucleic acids of the invention can be identified by conventional techniques. As used herein, a homolog to an Orc3N polypeptide is a polypeptide from a human or other animal that has a high degree of structural similarity to the identified Orc3N polypeptide, e.g. at least 95% amino acid sequence identity.

Identification of human and other organism homologs of Orc3N polypeptides will be familiar to those of skill in the art. In general, nucleic acid hybridization is a suitable method for identification of homologous sequences of another species (e.g., human, cow, sheep), which correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode Orc3N polypeptides identified herein to screen the library for related nucleotide sequences. The screening preferably is performed using high-stringency conditions to identify those sequences that are closely related by sequence identity. Nucleic acids so identified can be translated into polypeptides and the polypeptides can be tested for an Orc3N functional activity, (e.g. a viral-inhibition activity).

The term "high stringency" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Orc3N polypeptide nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecules and sequencing.

In general, Orc3N homologs and alleles typically will share at least 90% nucleotide identity and/or at least 95% amino acid identity to the sequences of Orc3N polypeptides or fragments thereof, and precursors thereof. Nucleic acid and polypeptides, respectively, in some instances will share at least 95% nucleotide identity and/or at least 97% amino acid identity, and in other instances will share at least 97% nucleotide identity and/or at least 99% amino acid identity. The percent identity can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for Orc3N polypeptide genes, a Southern blot may be performed using the foregoing conditions, together with a detectably labeled probe (e.g. radioactive or chemiluminescent probes). After washing the membrane to which the DNA is finally transferred, the membrane can be placed against X-ray film or a phosphorimager to detect the radioactive or chemiluminescent signal. In screening for the expression of Orc3N polypeptide nucleic acids, Northern blot hybridizations using the foregoing conditions can be performed on samples taken from viral-infected subjects (for example subjects with EBV) or subjects suspected of having a condition characterized by viral infection (e.g. EBV infection). Amplification protocols such as polymerase chain reaction using primers that hybridize to the sequences presented also can be used for detection of the Orc3N polypeptide genes or expression thereof.

Identification of related sequences can also be achieved using polymerase chain reaction (PCR) and other amplification techniques suitable for cloning related nucleic acid sequences. Preferably, PCR primers are selected to amplify portions of a nucleic acid sequence believed to be conserved (e.g., a catalytic domain, a DNA-binding domain, etc.). Again, nucleic acids are preferably amplified from a tissue-specific library.

The invention also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Orc3N polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions and deletions of one or more nucleotides (preferably 1–20 nucleotides that are useful for practicing the invention). In preferred embodiments, these modified nucleic acid molecules and/or the polypeptides they encode retain at least one activity or function of the unmodified nucleic acid molecule and/or the polypeptides, such as viral inhibition, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under high stringency conditions known to one of skill in the art.

For example, modified nucleic acid molecules that encode polypeptides having single amino acid changes can be prepared. Each of these nucleic acid molecules can have one, two, or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

Fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Fragments also can be used to produce fusion proteins for generating antibodies or determining binding of the polypeptide fragments, or for generating immunoassay components. Likewise, fragments can be employed to produce nonfused fragments of the Orc3N polypeptide, useful, for example, in the preparation of antibodies, and in immunoassays. The antibodies can be used, for example, to identify specific epitopes in Orc3N that are responsible for viral modulation. Preferred fragments are fragments that inhibit viral replication.

Fragments of a polypeptide preferably are those fragments that retain a distinct functional capability of the polypeptide. Functional capabilities that can be retained in a fragment of a polypeptide include the ability to inhibit viral replication. As will be recognized by those skilled in the art, the size of the fragment will depend upon factors such as whether the fragment is of sufficient size to inhibit viral replication. Thus, some fragments of Orc3N polypeptides will consist of-longer segments while others will consist of shorter segments, (e.g. 5, 6, 7, 8, 9, 10, 11 or 12 or more amino acids long, including each integer up to the full length of the Orc3N polypeptide). Those skilled in the art are well versed in methods for selecting functional fragments of polypeptides.

The skilled artisan will also realize that conservative amino acid substitutions may be made in Orc3N polypeptides to provide functionally equivalent variants, or homologs of the foregoing polypeptides, i.e, the variants retain the functional capabilities of the Orc3N polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the Orc3N polypeptides include conservative amino acid substitutions in the amino acid sequences of polypeptides disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. For example, upon determining that a peptide is an Orc3N-equivalent polypeptide, one can make conservative amino acid substitutions to the amino acid sequence of the peptide, and still have the polypeptide retain its specific viral replication inhibition characteristics.

Conservative amino-acid substitutions in the amino acid sequence of Orc3N polypeptides to produce functionally equivalent variants of Orc3N polypeptides typically are made by alteration of a nucleic acid encoding Orc3N polypeptides. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding an Orc3N polypeptide. Where amino acid substitutions are made to a small unique fragment of an Orc3N polypeptide, the substitutions can be made by directly synthesizing the peptide. The activity of functionally equivalent fragments of Orc3N polypeptides can be tested by cloning the gene encoding the altered Orc3N polypeptide into a bacterial or mammalian expression vector, introducing the vector into an appropriate host cell, expressing the altered polypeptide, and testing for a functional capability of the Orc3N polypeptides as disclosed herein. Peptides that are chemically synthesized can be tested directly for function, e.g., for inhibiting viral (e.g. EBV) replication.

Compositions of the various forms of the Orc3N nucleic acid molecules and polypeptides useful for practicing the invention are described herein. In general these compositions are prepared in the manner described in PCT publication number WO99/58673, the contents of which is in its entirety hereby incorporated by reference. To accomplish the various treatments as described herein, a nucleic acid that encodes Orc3N or a functional portion or domain thereof is introduced into a mammalian cell (e.g., mammalian somatic cell, mammalian germ line cell (sperm and egg cells)). This can be accomplished by inserting the isolated nucleic acid that encodes either the full length Orc3N polypeptide, or a functional equivalent thereof, into a nucleic acid vector, e.g., a DNA vector such as a plasmid, virus or other suitable replicon (e.g., a viral vector), which can be present in a single copy or multiple copies. The nucleic acid can be transfected or transformed into cells using suitable methods known in the art such as electroporation, microinjection, infection, and lipofection and direct uptake. Such methods are described in more detail, for example, in Sambrook et al., "Molecular Cloning: A Laboratory Manual," 2nd ED. (1989), Ausubel, F. M., et al., Current Protocols in Molecular Biology, (Current Protocol, 1994) and Sambrook et al., "Molecular Cloning: A Laboratory Manual," 2nd, ED. (1989).

Orc3N can be used to prevent and/or treat a viral infection by delivering to cells the Orc3N molecules, described herein, in vitro or in vivo. The cells to which Orc3N molecules may be delivered in vitro include, but are not limited to, cultured cells. Examples of cultured cells to which Orc3N may be delivered to prevent and/or treat a viral infection, include but are not limited to, cells used to produce recombinant proteins and cells to be transplanted into a subject (e.g. bone marrow, blood cells, kidney cells, corneal cells, liver cells and stem cells).

Orc3N molecules can be delivered to a cell in vitro or in vivo by the use of viral vectors comprising one or more nucleic acid sequences encoding an Orc3N polypeptide. Generally, the nucleic acid sequence has been incorporated into the genome of the viral vector. The viral vector containing Orc3N described herein or nucleic acid sequences encoding the Orc3N polypeptide can be contacted with a cell in vitro or in vivo and infection can occur. The cell can then be used experimentally to study, for example, the effect of Orc3N molecules on viral replication in vitro or the cells can be implanted into a subject for therapeutic use. The cell can be migratory, such as hematopoietic cells, or non-migratory. The cell can be present in a biological sample obtained from the subject (e.g., blood, bone marrow) and used in the treatment of disease, or can be obtained from cell culture and used to dissect viral replication pathways in in vivo and in vitro systems.

After contact with the Orc3N polypeptide or with the viral vector comprising a nucleic acid sequence encoding Orc3N, the sample can be returned to the subject or re-administered to a culture of subject cells according to methods known to those practiced in the art. In the case of delivery to a subject or experimental animal model (e.g., rat, mouse, monkey, chimpanzee), such a treatment procedure is sometimes referred to as ex vivo treatment or therapy. Frequently, the cell is removed from the subject or animal and returned to the subject or animal once contacted with the viral vector comprising the nucleic acids of the present invention. Ex vivo gene therapy has been described, for example, in Kasid, et al., *Proc. Natl. Acad. Sci. USA* 87:473 (1990); Rosenberg, et al, *New Engl. J Med.* 323:570 (1990); Williams, et al., *Nature* 310476 (1984); Dick, et al., *Cell* 42:71 (1985); Keller, et al., *Nature* 318:149 (1985) and Anderson, et al., U.S. Pat. No. 5,399,346 (1994).

Where a cell is contacted in vitro, the cell incorporating the viral vector comprising a nucleic acid sequence of Orc3N can be implanted into a subject or experimental animal model for delivery or used in in vitro experimentation to study cellular events mediated by Orc3N.

Various viral vectors can be used to introduce the Orc3N nucleic acid into mammalian cells. Viral vectors include retrovirus, adenovirus, parvovirus (e.g., adeno-associated viruses), coronavirus, negative-strand RNA viruses such as orthomyxovirus (e.g., influenza virus), rhabdovirus (e.g., rabies and vesicular stomatitis virus), paramyxovirus (e.g. measles and Sendai), positive-strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g. vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology,* Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

A preferred method to introduce nucleic acid that encodes Orc3N into cells is through the use of engineered viral vectors. These vectors provide a means to introduce nucleic acids into cycling and quiescent cells, and have been modified to reduce cytotoxicity and to improve genetic stability. The preparation and use of engineered Herpes simplex virus type 1 (D. M. Krisky, et al., *Gene Therapy* 4(10):1120–1125. (1997)), adenoviral (A. Amalfitanl, et al., *Journal of Virology* 72(2):926–933. (1998)), attenuated lentiviral (R. Zufferey, et al., *Nature Biotechnology* 15(9)871–875 (1997)) and adenoviral/retroviral chimeric (M. Feng, et al., *Nature Biotechnology* 15(9):866–870 (1997)) vectors are known to the skilled artisan.). In addition to delivery through the use of vectors, Orc3N nucleic acids may be delivered to cells without vectors, e.g. as "naked" nucleic acid delivery using methods known to those of skill in the art.

Various forms of the Orc3N polypeptide or nucleic acid, as described herein, can be administered and delivered to a mammalian cell (e.g., by virus or liposomes, or by any other suitable methods known in the art or later developed. The methods of delivery can be modified to target certain cells, and in particular, cell surface receptor molecules or antigens present on tumor cells. Methods of targeting cells to deliver nucleic acid constructs are known in the art. The Orc3N polypeptide can also be delivered into cells by expressing a recombinant protein fused with peptide carrier molecules, examples of which, though not intended to be limiting, are tat or antennapedia. These delivery methods are known to those of skill in the art and are described in U.S. Pat. No. 6,080,724, and U.S Pat. No. 5,783,662 the entire contents of which are hereby incorporated by reference.

An Orc3N polypeptide may be administered using other methods known in the art. For example, the mode of administration is preferable at the location of the target cells. As such, the administration can be intranasal (as in administering a vector expressing an Orc3N nucleic acid molecule). Other modes of administration (parenteral, mucosal, systemic, implant, intraperitoneal, etc.) are generally known in the art. The agents preferably are administered in a pharmaceutically acceptable carrier, such as saline, sterile water, Ringer's solution, and isotonic sodium chloride solution.

Additional agents, for example small chemicals, that mimic the action of Orc3N to inhibit viral replication may be identified by selecting an agent that inhibits a target molecule that is a nucleic acid or an encoded protein selected from the group consisting of Orc1, Orc2, Orc3, Orc4, Orc5, Orc6, and a binding partner thereof (e.g., CDC6, Cdt1, MCM protein) (e.g., an agent which selectively binds to any of the foregoing target molecule nucleic acids or proteins and inhibits its transcription/translation/functional activity); and contacting the selected agent with a cell under conditions wherein the cell undergoes viral replication in the absence of an inhibitor, wherein a selected agent which inhibits viral replication is a viral replication inhibitor. Agents that can be tested in this manner include library molecules, such as those described in US patents: U.S. Pat. No. 6,103,869 and U.S. Pat. No. 5,663,299.

The invention will be more fully understood by reference to the following examples. These examples, however, are merely intended to illustrate the embodiments of the invention and are not to be construed to limit the scope of the invention.

EXAMPLES

Example 1

Introduction

A 1.7-kb region of the EBV chromosome, oriP, supports the replication and maintenance of recombinant plasmids in human cells in the presence of a single EBV-encoded protein, EBNA-1 (Yates, J. L. et al., 313:812–5, 1985). Replication initiates at or near a 120-bp component of oriP called DS (for a dyad symmetry), which binds EBNA-1 and is the functional replicator of oriP (Gahn, T. A., and Schildkraut, C. L. *Cell* 58:527–35, 1989; Harrison, S. et al., *J Virol* 68:1913–25, 1994; Yates, J. L. et al., *J Virol* 74:4512–22, 2000). The second component of oriP, FR (for family of repeats), also binds EBNA-1 but functions differently, providing for the stability of episomes by tethering them to human chromosomes during mitosis (Hung, S. C. et al., *Proc Natl Acad Sci USA* 98:1865–1870, 2001; Krysan, P. J. et al., *Mol Cell Biol* 9:1026–33, 1989; Marechal, V. et al., *J Virol* 73:4385–92, 1999; Simpson, K. et al., *Mol Cell Biol* 16:5117–26, 1996). Because EBNA-1 appears to lack enzymatic activity (Frappier, L., and O'Donnell, M. *J Biol Chem* 266:7819–260, 1991; Middleton, T., and Sugden, B. *J Virol* 66:489–95, 1992), initiation of DNA replication at oriP may rely on cellular proteins. Plasmids bearing oriP reportedly are replicated no more than once per cell cycle (Yates, J. L., and Guan, N. *J Virol* 65:483–8, 1991). We believe that the plasmids are controlled by replication licensing. In addition, plasmids containing oriP and expressing EBNA1 reportedly replicate in human but not in rodent cells. We believe there is a requirement of a host cell-specific factor (Wysokenski, D. A., and Yates, J. L. *J Virol* 63:2657–66, 1989).

Methods

Orc2 Targeting Construct and Screening for Recombinants

A promoterless strategy was adapted for targeting the Orc2 gene (Waldman, T. et al., *Cancer Res* 55:5187–90, 1995). A BAC clone (GenBank Accession No. AC005037) containing human Orc2 was obtained from Genome Sequencing Center at Washington University (St. Louis, Mo.) and used as the source for homologous arms. The two PCR amplified fragments, one 3.8-kb and the second 1.0-kb, were used to construct the 5' and 3' arms of the targeting vector, respectively. The 3.8-kb subclone contained the region immediately 5' of the initiation codon located in exon 3 of Orc2 coding region. The 1.0-kb subclone contained a region beginning 72-bp distal to the initiation codon. Two fragments were assembled in pKO plasmid (Stratagene, La Jolla, Calif.) surrounding promoterless geneticin-resistant gene containing simian virus 40 polyadenylation signals (Neo cassette) (FIG. 1A). loxP sites surrounding the Neo cassette were incorporated into the vector. This strategy allowed Cre-mediated excision of the Neo cassette after targeting of the first allele and thus the use of the same targeting vector. For first allele targeting, G418-resistant clones were screened by genomic Southern blotting with a hybridization probe located immediately outside the 3' homologous arm and geneticin resistant gene coding region (FIG. 1A). A clone carrying a homologous recombinant and no additional random integrants was then infected with recombinant adenovirus expressing Cre recombinase (purchased from Gene Transfer Vector Core, University of Iowa, Iowa City, Iowa) to yield G418-sensitive clones. One of these heterozygous clones without Neo (+/−Cre) was then used for second round homologous recombination. Genomic DNA was prepared from G418-resistant clones and analyzed by PCR using primers "a" (5'-agctaccttgattggatttagctc; SEQ ID NO: 7) and "c" (5'-acctccttctctatctagaatgtg; SEQ ID NO: 8) (FIG. 1C), yielding 352- and 313-bp fragment for +/−Cre, a 352-bp for +/−, a 313-bp for del/−. EcoRI digestion of PCR product was performed to confirm that the PCR products were derived from Orc2 locus (FIG. 1D). Homologous recombinants identified by PCR were confirmed by Southern blot and several clones with both alleles of Orc2 disrupted were obtained and used for further experiments.

Western Blot Analysis, Immunoprecipitation and Chromatin Fraction Preparation.

Lysates of log-phase cells were used. Equal amounts of protein were loaded for blotting. Orc2 antibody was raised against a recombinant His6-tagged fragment of human Orc2 (27–577 amino acids) (Quintana, D. G., et al., *J Biol Chem* 272:28247–51, 1997). Conditions for immunoprecipitation and immunoblotting have been described (See: Dhar, S. K., and Dutta, A. *J Biol Chem* 275:34983–8, 2000; Thome, K. C. et al., *J Biol Chem* 275:35233–41, 2000). Cells were lysed in CSK buffer (100 mM NaCl, 2 mM MgCl$_2$), and the chromatin pellet extracted with DNase I and CSK buffer (200 mM NaCl, 2 mM MgCl$_2$) to prepare the chromatin fraction (See: Tatsumi, Y., et al., *J Biol Chem* 275:5904–10, 2000). At least two independent experiments were carried out for each condition.

Cell Proliferation and Cell Cycle Analysis

To measure the cell proliferation and viability, equal number of cells were plated for wild type and /– and monitored by counting the cells after trypan blue treatment or MTT-based colorimetric assay (Roche Molecular Biochemicals, Indianapolis, Ind.). Cells synchronized to G1-S by 0.4 mM mimosine (Sigma, St Louis, Mo.) for 24 h were released and the passage of cells through S phase followed by one-hour pulse labeling with [$^3$H]thymidine every 3 h after release. Standard methods were used for flow-cytometry analysis and FlowJo software (Tree Star Inc., San Carlos, Calif.) used for estimation of percentage of cells in various phases of the cell cycle.

Assay for EBV Plasmid Replication and Maintenance.

For long-term replication assay, cells were washed extensively the day after transfection and $\frac{1}{10}^{th}$ of the cells returned to culture. Medium containing hygromycin B (Life Technologies Inc, [GIBCO BRL], Rockville, Md.) 50–100 μg/ml was added the next day and resistant cells selected for up to 10 days. After selection, hygromycin B-resistant colonies were stained by crystal violet or used for alkaline plasmid preparation. p220.2 is identical to p201 (Yates, J. L., et al., *Nature* 313:812–5, 1985) except that it contains a polylinker nearly 400 bp to the right of oriP.

For the transient replication assay, plasmids p367 (functional EBNA-1) and p396 (deletion in the EBNA-1 DNA-binding domain) have been described (Yates, J. L., and Camiolo, S. M. (1988). Dissection of DNA replication and enhancer activation functions of Epstein-Barr virus nuclear antigen 1. In Cancer Cells, B. S. a. T. Kelley, ed. (Cold Spring Harbor, N.Y., Cold Spring Harbor Laboratory Press), pp. 197–205). p367ΔO lacks DS of oriP (deletion, 8995–9123 of EBV). Plasmids were extracted using the alkaline lysis procedure 96 h after transfection (Yates et al., 2000). For each experiment on transient replication, an equivalent amount of bacterially derived plasmid DNA was mixed with genomic DNA from mock transfected cells and digested with DpnI and run in parallel to ensure that all DpnI-sensitive DNA was properly digested. The plasmids without functional EBNA1 (p396) or DS of oriP (p367ΔO) did not replicate in the WT cells, confirming that both EBNA1 and the replicator of oriP are necessary for oriP-dependent plasmid replication in the HCT116 cell line.

The adenovirus expressing wild-type Orc2, was constructed as follows: the pShuttle vector was linearized using NheI and then end filled using Klenow and digested with NotI. The Orc2 reading frame insert was released from pGEX-5x-3 ORC2 using SmaI and NotI and then ligated to pShuttle vector. The pShuttle vector is a component of Adeno-X Expression system (CLONTECH Laboratories, Inc. Palo Alto, Calif.). The construction of the pEBG-Geminin expression vector, was performed as follows: Geminin wild-type ORF (derived from GenBank Ace. No XM_004261 was PCR amplified using primers (having SpeI restriction enzyme site in the forward primer and NotI site in the reverse primer). The PCR product was digested with SpeI and NotI followed by ligation at the SpeI and NotI sites of the pEBG vector. pEBG has been described in Mayer, B. J. et al., *Curr. Biol.* 5:296–305, 1995.

The construction of the pEBG-Geminin(ΔD) expression vector, was performed as follows: Geminin ΔD-Box ORF was obtained from Geminin wild-type ORF by using standard mutagenesis protocol (see: *Molecular Cloning: A Laboratory Manual*, J. Sambrook, et al., eds., Second Edition, Cold Spring Harbor Laboratory Press, Cold Spring Harbor, N.Y., 1989). The resultant ORF was PCR amplified using primers (having SpeI and NotI sites in the forward and reverse primers respectively). The PCR product was digested with SpeI and NotI followed by ligation at SpeI and NotI sites of pEBG. pEBG has been described in Mayer, B. J., et al., *Curr. Biol.* 5:296–305, 1995.

For the rescue of oriP expression in Δ/–cells, the cells were infected with high-titer adenovirus for 1 h, the medium changed and the cells transfected with p367 1 h later. Cellular DNA was harvested at 96 h to assess plasmid replication. To study the effect of geminin, the plasmids (pEBG and derivatives) were co-transfected with p367 at a ratio of 2:1.

Results

Mutation of ORC2.

Homologous recombination was utilized to replace the third exon of ORC2 (encoding the initiator ATG) in HCT116 colon carcinoma cells with a Neomycin phosphotransferase (NEO) gene resulting in the expression of NEO from the endogenous ORC2 promoter (FIG. 1A). ORC2 +/–clones were identified in 2–3% of G418-resistant colonies by genomic Southern blot (FIG. 1B). Cre-mediated recombination of the loxP sites flanking the NEO gene excised the NEO cassette, made the cells susceptible to G418, and left a loxP site in place of most of exon 3 in the allele called Δ-ORC2. (FIG. 1C; Δ/+).

The second allele of ORC2 was targeted with the same targeting vector followed by selection in G418. Re-targeting of the loxP marked allele (Δ) re-created the—allele in cells called –/+ (FIG. 1C). PCR screening of genomic DNA with the indicated primers produced a 352-bp product from the +allele that was cut by EcoRI into fragments of 204 and 148 bp. Targeting of the wild-type ORC2 allele, on the other hand, created the desired cell-line (Δ/–) (FIG. 1C). PCR screening produced a 313-bp product from the Δallele that was cut by EcoRI into fragments of 204 and 109 bp. PCR analysis identified 8.8% of the G418-resistant clones as Δ/–mutants at the ORC2 locus (FIG. 1D, Δ/–). Single copy integration of the NEO cassette was confirmed by Southern blot.

The Δ-ORC2 Allele Produces a Low Level of an N Terminally Truncated Orc2 Protein.

Figure 2:
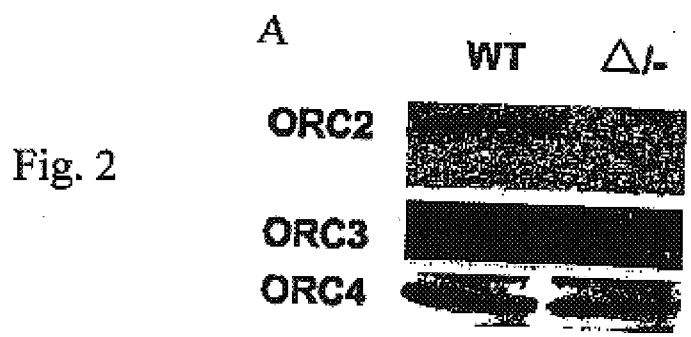
FIG. 2 shows biochemical characterization of ORC in the Δ/−cells.
Figure 2:
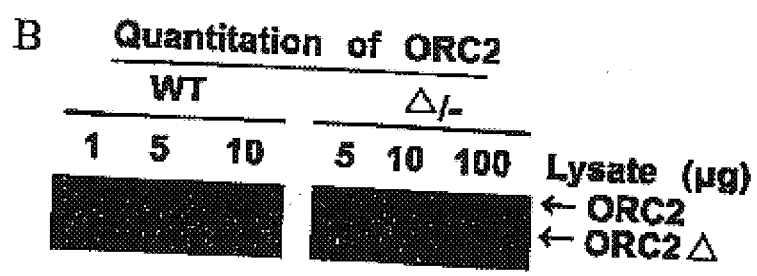
Figure 2:
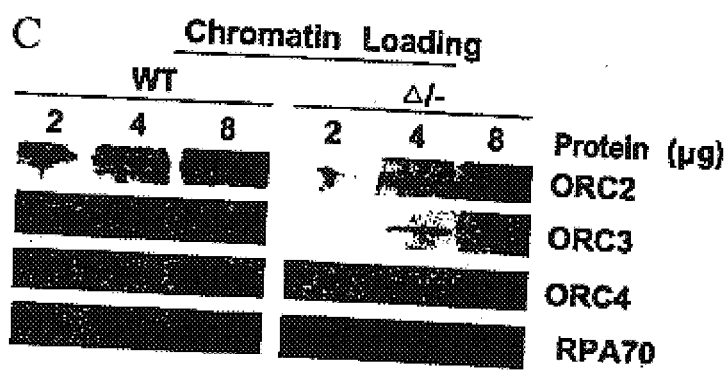
Figure 2:
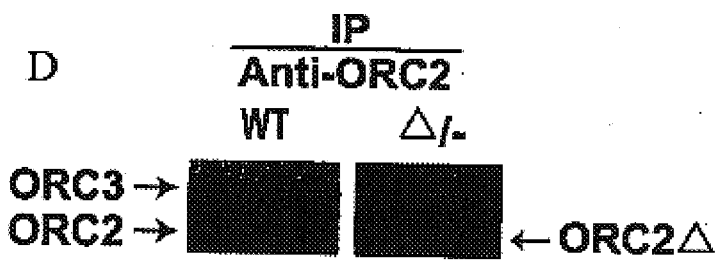

In a conventional gene-deletion experiment, transcription and polyadenylation of the drug-resistance cassettes inserted in the two alleles of the target gene prevents residual expression of the latter by blocking read-through transcription or alternative splicing. In the strategy employed herein, however, only a loxP site was left in the middle of exon 3 in the Δ allele. Although the initiator ATG was removed, low levels of a variant ORC2 mRNA produced by read-through transcription or alternative splicing could express an N terminally deleted Orc2 protein from methionine-74 encoded by exon 4. Although an antibody against amino acids 27–577 of Orc2 did not recognize any full-length 72 kD Orc2 protein in the Δ/–cells (FIG. 2A), an Orc2 related polypeptide of 68 kD was detected when 10 times more cell lysate was loaded for immunoblotting (FIG. 2B). Because the 68 kD polypeptide (ΔOrc2) was seen only in cells with the Δ-ORC2 allele, and because the public human genome database (National Center for Biotechnology Information) does not reveal any other gene-related to ORC2, the polypeptide was likely the product of the loxP marked Δ-ORC2 locus. Biochemical data (shown below) confirmed that ΔOrc2 associates with Orc3, emphasizing that it is derived from the Δ-ORC2 allele.

Effect of the Hypomorphic Mutation in ORC2 on the Other ORC Subunits.

The Δ/−cells express ΔOrc2 protein at 10% of the level of full-length Orc2 seen in wild-type (WT) HCT116 cells. The level of Orc4 was unchanged in the Δ/−cells, while that of Orc3 was decreased significantly (see FIG. 2A). The mRNA of ORC3 was expressed at normal levels in the Δ/−cells, suggesting that the decrease of Orc3 protein is due to post-transcriptional mechanisms. Orc3 binds directly to Orc2 in vitro and in recombinant expression systems and all the cellular Orc3 and Orc2 co-eluted with each other as a 150 kD complex in a gel-filtration column (Thome, K. C., et al., *J Biol Chem* 275:35233–41, 2000). Therefore, Orc2 and Orc3 are normally bound to each other. The decrease in ΔOrc2 protein in the Δ/−cells probably results in free Orc3 that is unstable, accounting for the decrease of the latter in these cells.

Immunoblotting different concentrations of protein from the chromatin fraction of cells indicated that the amounts of chromatin-associated ΔOrc2 and Orc3 were decreased to less than 25% in the Δ/−cells (FIG. 2C). Therefore, the decrease in total cellular ΔOrc2 and Orc3 was accompanied by a decrease in the amount of the two proteins loaded on chromatin. Although Orc2 and Orc3 are associated with each other in human somatic cells, Orc4 readily dissociates from the complex in cell extracts (see Dhar, S. K., and Dutta, A. *J Biol Chem* 275:34983–8, 2000; Thome, K. C. et al., *J Biol Chem* 275:35233–41, 2000). If the Orc4 subunit is loaded on the chromatin individually, independent of Orc2, the level of chromatin bound Orc4 might not be decreased in the Δ/−cells. Chromatin associated Orc4, however, was also decreased to less than 25% suggesting that Orc2 and Orc3 are necessary for Orc4 to bind to chromatin (FIG. 2C). The DNA replication and repair factor, RPA70, is loaded on the chromatin to normal levels in the Δ/−cells providing a positive control for recovery of chromatin in these cells.

The enrichment of Orc3 and ΔOrc2 in the chromatin fraction of Δ/−cells allowed testing of whether the two were associated with each other. ΔOrc2 was immunoprecipitated by anti-Orc2 antibody and co-immunoprecipitated with Orc3, supporting the hypothesis that it is derived from the Δ-ORC2 locus (FIG. 2D). The N terminal 351 amino acids of Orc2 were dispensable for the association of Orc2 with Orc3 in vitro consistent with the association of ΔOrc2 (missing the N terminal 73 amino acids) with Orc3 in vivo. In this experiment, too, chromatin-associated ΔOrc2 and Orc3 were decreased relative to chromatin-associated Orc2 and Orc3 in +/+cells. A conservative estimate is that the chromatin associated ORC is decreased by at least 75% in the Δ/−cells.

The Hypomorphic Mutation in ORC2 Prolongs G1 Phase of the Cell-Cycle.

Figure 3:
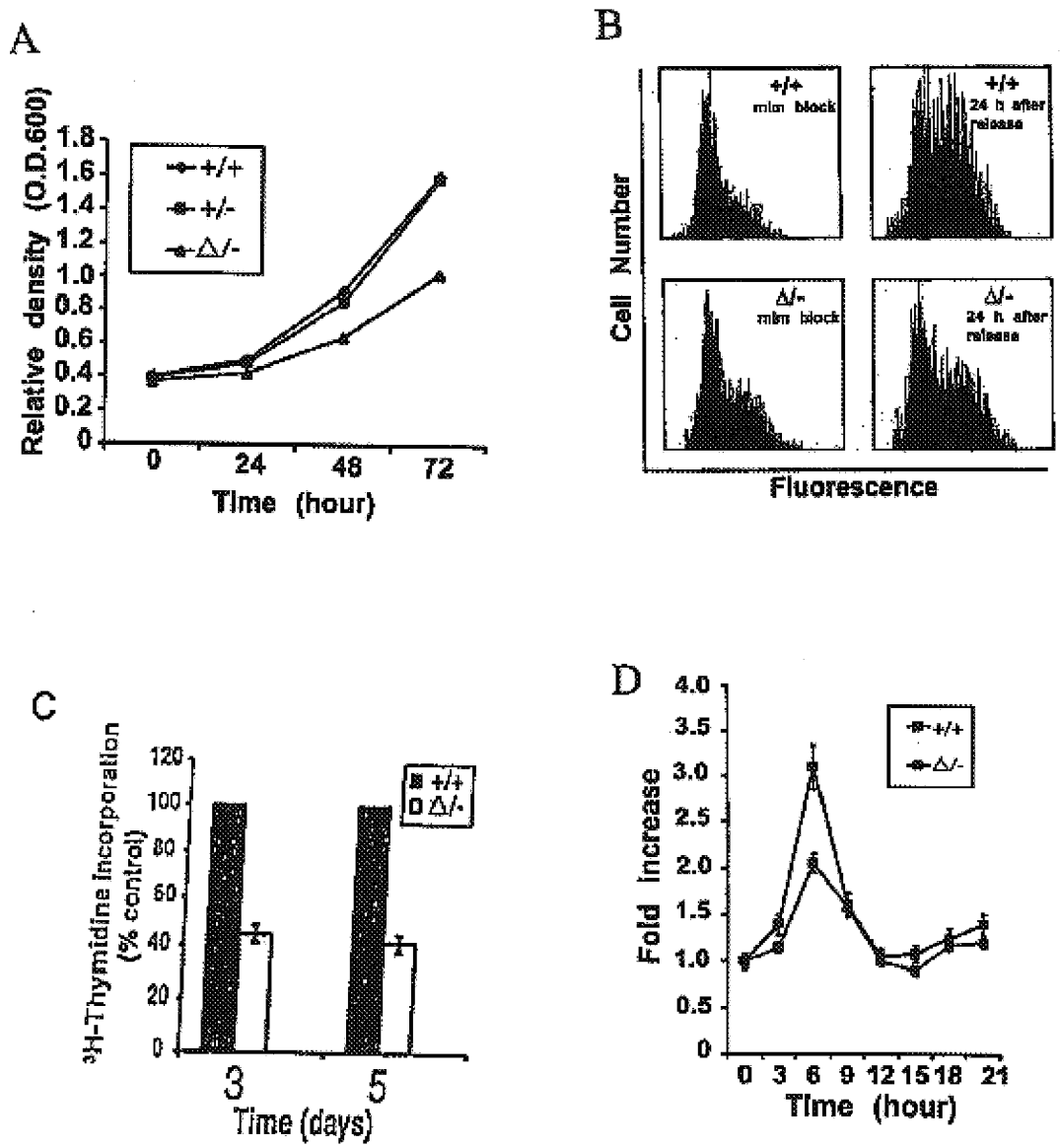
FIG. 3 graphs indicating ORC2 Δ/−cells are compromised in cell proliferation.

The proliferation rate of the ORC2 Δ/−cells was decreased by 30% (doubling time 43 hours versus 33.5 hours in ORC2 +/+ or +/−cells) (FIG. 3A). There was no increase in apoptosis or senescence in the Δ/−cells. FACS to measure the DNA content of asynchronously growing cells indicated a moderate increase in the G1 phase population in the Δ/−cells (Table 1) suggesting a relative prolongation of G1. Consistent with this finding, the percentage of cells entering S phase in Δ/−cells in the 24 hr following release from a mimosine-induced G1-S block (Gilbert, D. M., et al., *J Biol Chem* 270, 9597–606, 1995) is about half that in the +/+cells (wild type or WT) (FIG. 3B). $^3$H-thymidine incorporation in Δ/−cells over 3 or 5 day-intervals was also about half that of WT cells (FIG. 3C). $^3$H thymidine incorporation in cultures released from a mimosine-induced G1-S block showed that the height of the incorporation curve is decreased to 60–70% without any change in the width of the curve (FIG. 3D). Therefore, fewer cells enter S phase when Orc2 activity is compromised, but DNA replication is normal once the cells enter S phase so that the duration of S phase is unchanged. The decrease in proliferation rate of the Δ/−cells is the first direct evidence that Orc2 protein (and ORC, by extension) is necessary for normal proliferation of mammalian somatic cells.

TABLE 1

% of cells in different phases of the cell-cycle (mean and standard deviation of 3 determinations for WT cells and 6 determinations for Δ/− cells).

| HCT116 cells | G1 | S | G2/M |
|---|---|---|---|
| WT | 24.4 (1.2) | 51.7 (1.9) | 23.9 (1.1) |
| Δ/− | 33.8 (3.2) | 42.2 (1.6) | 24.0 (2.3) |

The Hypomorphic Mutation in ORC2 Impairs Replication From the oriP of EBV

To test whether cellular Orc2 is required to support EBV replication, a plasmid carrying oriP, EBNA-1 and a hygromycin resistance gene (p220.2) was transfected into WT and Δ/−cells. The results indicated that Orc2 Δ/−cells are unable to support DNA replication from oriP of Epstein Barr Virus and this defect is rescued by expression of wild-type Orc2. The experiment illustrated establishment of drug-resistant colonies of WT and Δ/−cells after transfection of plasmid p220.2 carrying EBV oriP, EBNA-1 and the hygromycin resistance marker or of pBabe-Puro expressing the puromycin resistance marker but lacking oriP and EBNA-1. Following selection in hygromycin or puromycin colonies were visualized by staining with crystal violet Replication of p220.2 allowed hygromycin-resistant colonies to emerge in the WT cells but not in the Δ/−cells. DpnI-resistant plasmids were recovered from these colonies indicating that the transfected plasmids had replicated in the WT cells (FIG. 4A, lane 1). pBabe-Puro, a plasmid that does not have oriP or EBNA-1 and is integrated in the host cell chromosome was used as a control. Transfection of pBabe-Puro produced the same number of puromycin-resistant colonies in WT and Δ/−cells. Therefore, the +/+ and Δ/−cells do not appear to be inherently different in their efficiency of transfection or expression of drug resistance markers.

To confirm that the Δ/−cells did not support replication from oriP, a transient replication assay was performed (FIG. 4A). p367 (with wild-type oriP and expressing EBNA-1) (Yates, J. L., et al., *J Virol* 74:4512–22, 2000) was transfected into WT and Δ/−cells. 96 h after transfection, DpnI-resistant (replicated) plasmids were detected when p367 was transfected in WT cells but not in Δ/−cells (FIG. 4A, lanes 6 and 7), suggesting that Orc2 was necessary for replication from oriP of EBV.

Figure 4:
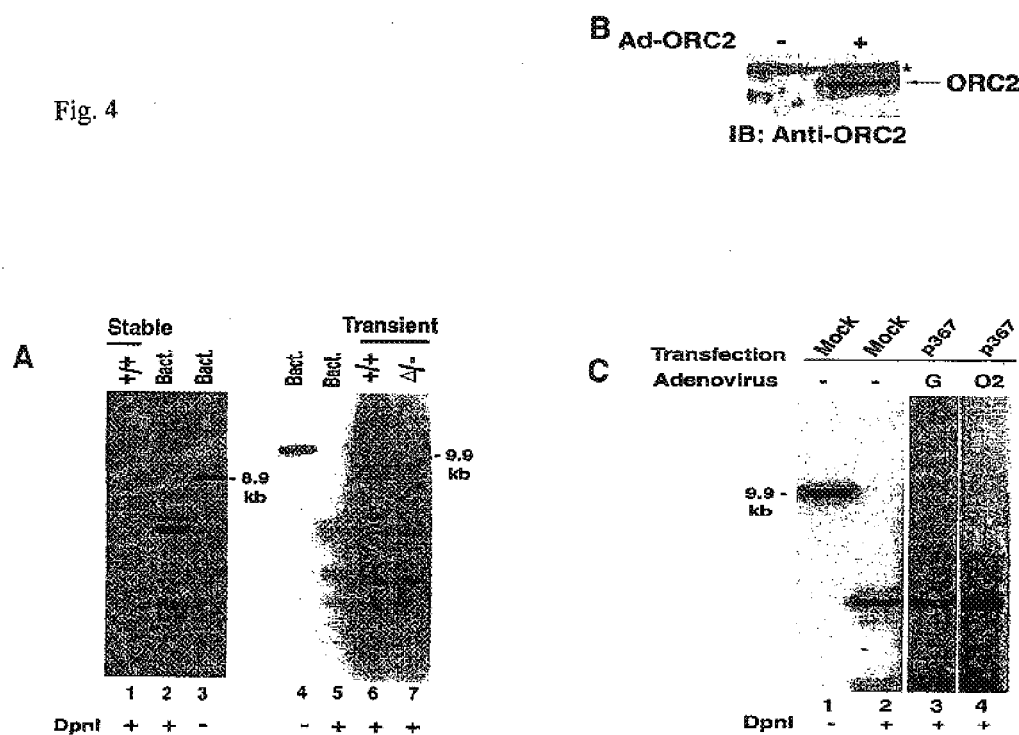
FIG. 4 shows graphs indicating Orc2 Δ/−cells are unable to support DNA replication from oriP of Epstein Barr Virus and this defect is rescued by expression of wild-type Orc2.

If the defect in OriP based plasmid replication in Δ/−cells is due to the mutation in ORC2, expression of wild-type Orc2 protein should rescue the replication defect. This experiment was done by Adenovirus vector mediated transient expression of Orc2. Infection of HCT116 Δ/–cells with an adenovirus vector that expresses Orc2 resulted in the reappearance of wild type 72 kD Orc2 protein in the cell extracts (FIG. 4B). Following infection with Adeno-Orc2 or with negative control Adeno-GFP (expressing Green fluorescent protein) the HCT116 Δ/–cells were transfected with p367 (FIG. 4C). The detection of DpnI resistant plasmid DNA in lane 4 (compared to lane 3) indicates that restoration of wild type Orc2 protein in the Δ/–cells restored replication from OriP.

Geminin Inhibits Replication From oriP of EBV

Figure 5:
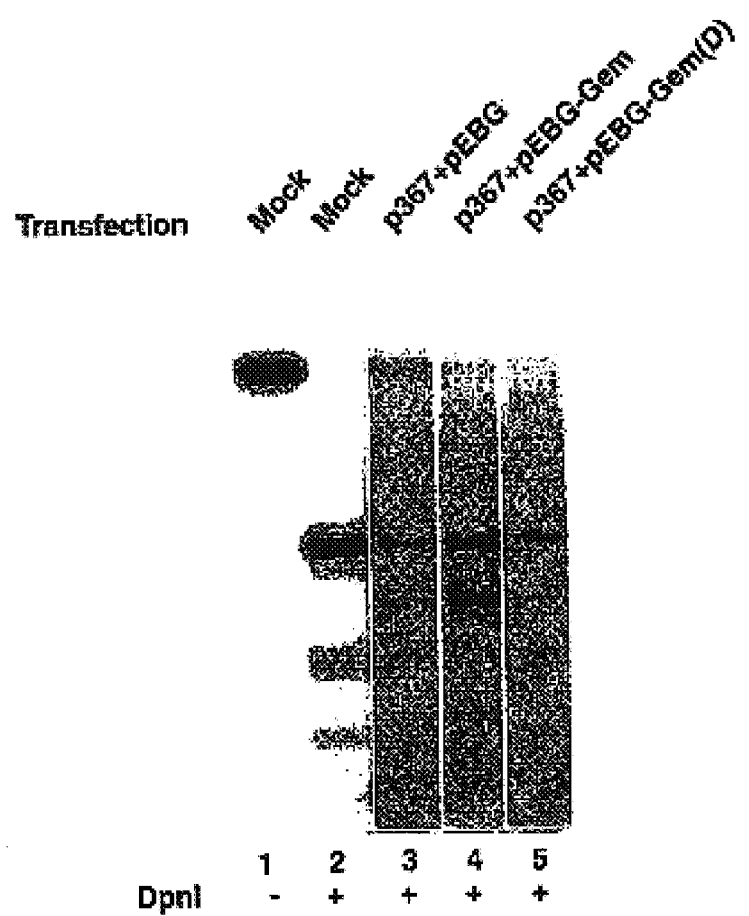
FIG. 5 illustrates that Geminin inhibits replication of EBV based episome. Southern blot to detect DpnI resistant p367 plasmids that have replicated in HCT116 +/+cells following co-transfection with plasmids expressing GST (lane 3), GST-geminin (lane 4) and GST-geminin-ΔDB (lane 5). Lanes 1 and 2 are the same as in FIG. 4C.

If ORC is required for replication from oriP, other components of the replication initiation complex might also be required. Geminin, a regulator of the cell cycle, has been shown to interact with one of these downstream components, Cdt1, to prevent the loading of MCM proteins (Wohlschlegel, J. A., et al., Science 290, 2309–12, 2000). Geminin is degraded by the anaphase promoting complex and can be stabilized in the cell by mutation of a specific destruction box (gemininΔDB) (McGarry, T. J. and Kirschner, M. W. Cell 93:1043–53, 1998). p367 (a plasmid containing oriP and EBNA1) was co-transfected into HCT116 cells with plasmid pEBG expressing glutathione S transferase (GST) as control or with plasmids expressing GST-geminin or GST-gemininΔDB (FIG. 5). Judging from the amount of DpnI-resistant replicated plasmid DNA, GST-geminin inhibited replication of p367 (lane 4). GST-gemininΔDB, which expresses a higher concentration of the protein, inhibited replication from p367 to a greater extent (lane 5). Therefore, proteins like Cdt1 and MCM, initiation factors downstream from ORC, are also likely to play a role in DNA replication from oriP.

Example 2

Introduction

Because genetic experiments are difficult to perform in mammalian systems, the human Origin Recognition Complex (ORC) subunits have not been shown to have a role in replication or cell proliferation. Utilizing knowledge learned about the architecture of the human ORC, a dominant negative ORC subunit was created, which was designed to disrupt the formation of endogenous ORC. Overexpression of this dominant negative ORC subunit blocked the cell cycle in G1, providing the evidence of the importance of ORC in cell proliferation.

Methods

Plasmid Constructions

Cloning of ORC1-6 cDNAs are described elsewhere (Gavin, K. A., et al., Science 270:1667–71, 1995; Pinto, S., Quintana, D. G., et al., Neuron 23,:45–54, 1999; Quintana, D. G. et al., J Biol Chem 272:28247–51, 1997; Quintana, D. G., et al., J Biol Chem 273:27137–45, 1998; Dhar, S. K. & Dutta, A. J Biol Chem 275:34983–8, 2000). Coding sequences of ORC1, ORC4, ORC5, ORC6 and ORC3N200 were cloned into pFastBac (Life Technologies, GIBCO BRL) and coding sequences of ORC2 and ORC3 were cloned into pFastBac Dual. ORC2, 4 and 5 were also cloned in pFB-GST vectors to express GST fusion proteins. ORC3 and all the related constructs for in vitro transcription and translation reactions were made into T7T3DPAC vector (Acc. No. U13871). Full length and C-terminal ORC2 fragments were cloned into pGEX-5X-3 (Invitrogen Corp., Carlsbad, Calif.) to produce bacterial fusion proteins. Description of construct preparation provided above. (see Example 1).

Expression of ORC Subunits in Insect Cells, Purification and Gel Filtration

Baculoviruses were produced from the recombinant pFastBac or pFB-GST plasmids using the Bac-to-Bac expression system (Life Technologies, GIBCO BRL). Hi5 or Sf9 cells (Invitrogen Corp.) were infected with these baculoviruses according to the manufacturers' recommendations. Cells were harvested 48 hours post-infection. The cell pellet was washed once in cold phosphate buffered saline (PBS), and subsequently resuspended in hypotonic lysis buffer (10 mM Tris.Cl, pH 7.9; 10 mM KCl; 1.5 mM $MgCl_2$; 1 mM Phenylmethylsulfonyl Fluoride (PMSF); 2 μg/ml pepstatin; 2 μg/ml leupeptin; 5 μg/ml aprotinin; 1 mM DTT). The cell suspension was homogenized in a Dounce homogenizer using a B-type pestle followed by centrifugation at 3000 rpm for 7 min. The pellet containing the nuclei was lysed in buffer H/0.15 (50 mM HEPES.KOH, pH 7.5; 150 mM KCl; 0.02% NP-40; 5 mM Magnesium acetate; 1 mM EDTA; 1 mM EGTA; 10% glycerol, 1 mM PMSF, 2 μg/ml pepstatin, 2 μg/ml leupeptin, 5 μg/ml aprotinin, 1 mM DTT). The resulting suspension was subjected to ammonium sulfate precipitation (starting with 10% followed by 30% and finally 50%). The pellet following 50% ammonium sulfate cut was resuspended in buffer H/0.0 (no salt) and then dialyzed overnight against buffer H/0.15. The dialyzed sample was then bound to GST beads (Sigma-Aldrich, St. Louis, Mo.), washed three times with buffer H/0.25. Proteins were eluted using reduced glutathione elution buffer (50 Mm Tris.Cl, pH 8.0; 20 mM reduced glutathione; 0.01% NP-40; 100 mM NaCl). Gel filtration of glutathione eluate using fast protein liquid chromatography Superose 12 (Amersham Pharmacia Biotech Inc, Piscataway, N.J.) column was performed as described previously (Dhar, S. K. & Dutta, A. J Biol Chem 275:34983–8, 2000).

Cell Culture, Transfection, Immunoblotting, Immunoprecipitation and Silver Stain.

Sf9 and Hi5 cells were maintained according to the manufacturers' protocol (Invitrogen). U2OS cells used for FACS analysis were maintained in Dulbecco's Modified Eagle Medium (DMEM) with 10% fetal bovine serum (Life Technologies, GIBCO BRL). Plasmid DNA used for transfection were purified using QIAGEN maxiprep kits. Cells were grown in 100 mm dishes and transfected using Lipofectamine (Life Technologies, GIBCO BRL). Western blotting and immunoprecipitation techniques were carried out using standard protocols. Anti-GST polyclonal antibodies were purchased from Santa Cruz Biotechnology Inc, Santa Cruz, Calif. Antibodies against HsORC1-6 have been described previously (Pinto, S., et al., Neuron 23:45–54, 1999; Quintana, D. G. et al., J Biol Chem 272:28247–51, 1997; Quintana, D. G. et al., J Biol Chem 273:27137–45, 1998; Dhar, S. K. and Dutta, A. J Biol Chem 275:34983–8, 2000). Silver staining was performed as described in (Dunn, M. J. and Crisp, S. J. Methods Mol Biol 32:113–8, 1994).

In vitro Transcription and Translation (IVT) Reactions, GST Pull Down Assay.

IVT reactions to produce $^{35}$S methionine labeled full length and different deletions of ORC3 were performed using the Promega TNT system (Madison, Wis.). Pull-down assays on glutathione agarose beads were done as described in (Lin, Y. L., et al., J Biol Chem 271:17190–8, 1996).

FACS Analysis

U2OS cells were transfected with farnesylated GFP (CLONTECH Laboratories, Inc., Palo Alto, Calif.) alone or in combination with FLAGORC2, GFPC1-ORC3N or GFPC1-ORC3C1. Forty-eight hours following transfection, cells were trypsinized, washed with phosphate buffered saline (PBS), fixed with cold 70% ethanol and stored until further use. Before analysis, fixed cells were resuspended in PBS containing 50 μg/ml propidium iodide (Sigma-Aldrich), 10 μg/ml RnaseA (Sigma-Aldrich) and 0.05% Noniodet P-40 and then incubated for 1 hour at 4° C. Cells were then washed in PBS and analyzed by flow cytometry.

The data was further analyzed using FLOWJO software (Tree Star Inc.) to calculate the percentage of cells residing in different cell cycle stages.

Results

1. GSTORC5, 2, 3 and 4 forms a Complex

Figure 6:
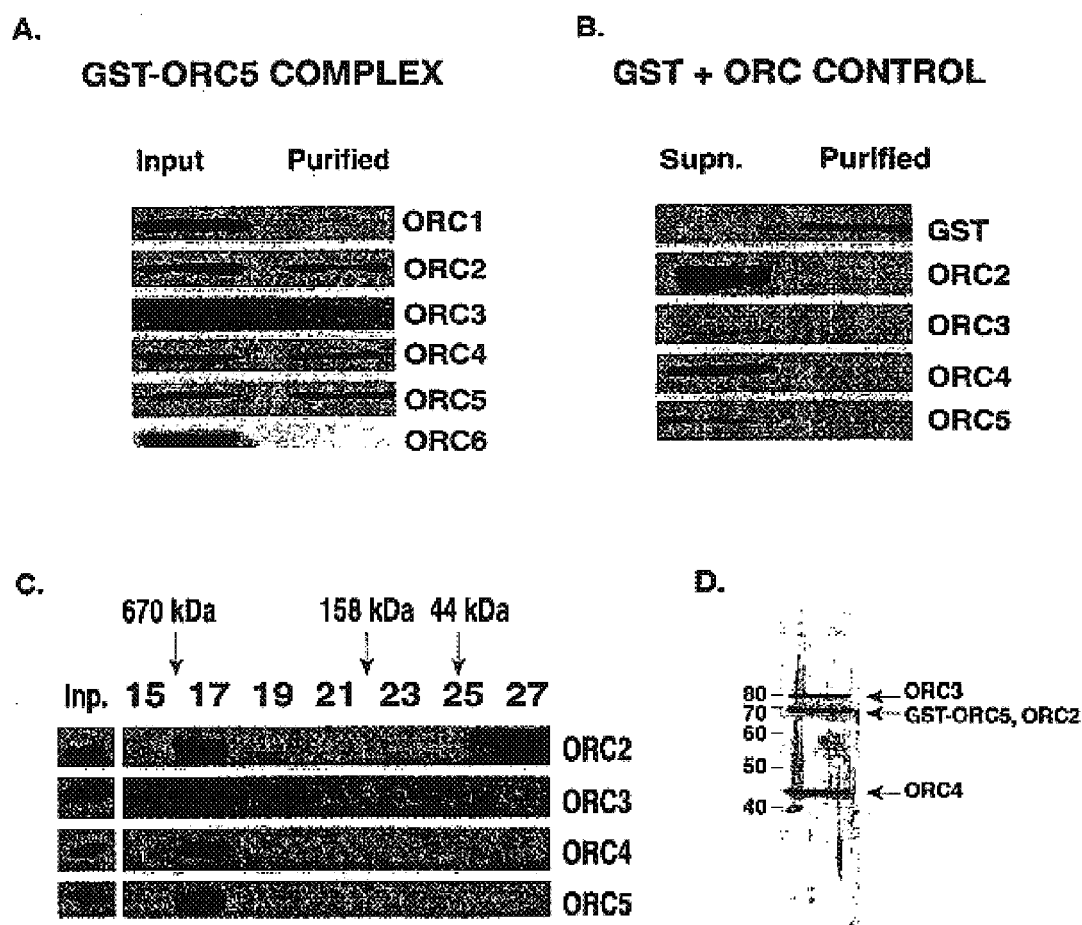
FIG. 6 shows immunoblots of Human ORC2-5 co-purifying in a complex.

ORC2, 3, 4 and 5 subunits have been shown to interact with each other in human cell extracts (Dhar, S. K. and Dutta, A. J Biol Chem 275:34983–8, 2000). To purify recombinant six protein human origin recognition complex, Sf9 insect cells were infected with baculoviruses expressing human ORC1-6 subunits. One of the subunits, ORC5 was GST tagged. Following pull down on glutathione beads, it was determined that GSTORC5, 2, 3 and 4 could be purified as a complex (FIG. 6A). ORC1 did not enter into the complex in a stoichiometric ratio and the presence of very little ORC1 in FIG. 6A was not reproducible in different preparations. ORC6 did not enter into the complex at all. Both ORC1 and ORC6 were expressed at a high level. In a control experiment, GST was expressed alone with other ORC subunits. Pull down on glutathione beads purified only GST but none of the ORC subunits. The results shown in FIG. 6A indicate the formation of a complex of ORC2, 3, 4 and 5 and are not due to precipitation of the proteins on the glutathione beads. GST pull down experiments using GST tags on different ORC subunits (GSTORC2 and GSTORC4) confirmed the previous result showing ORC2, 3, 4 and 5 form a core complex.

To further show that GSTORC5, 2, 3 and 4 subunits are in one complex, the elution pattern of these proteins upon gel filtration was analyzed. Proteins were eluted from the GST beads using reduced glutathione and subsequently passed through a Superose 12 gel filtration column. Upon western blotting of different fractions with different anti-ORC antibodies, GSTORC5, 2, 3, and 4 subunits were co-eluted in one fraction (FIG. 6C). The molecular mass of this complex was approximately 500 kDa, which is more than the combined molecular mass of the four ORC subunits. This may be because of the multimerization of the GST moieties to give a high molecular mass complex, or because the complex has an a typical shape. Silver staining of the purified protein used for the gel filtration experiment indicated that GST-ORC5, ORC2, 3, and 4 were the only proteins present in the preparation in significant amounts (FIG. 6D).

2. ORC2 and ORC3 Physically Interact with Each Other

Figure 7:
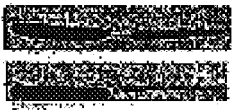
FIG. 7 shows immunoblots demonstrating direct interaction between ORC2 and ORC3 subunits. Baculovirus-expressed pairs of ORC subunits in each case (GSTORC2+3, GSTORC5+3, GSTORC5+4, GSTORC5+2, GSTORC4+2 and GSTORC4+3) are shown. Proteins bound to GST beads were immunoblotted using either anti-GST antibody or respective anti-ORC antibodies. 5% of the total lysate was loaded in the input lanes.

To determine which of the four interacting subunits interact directly, Sf9 insect cells were infected with six different combinations of baculoviruses expressing two ORC subunits in each case. One of the two viruses was GST tagged. Affinity purification on glutathione beads showed that only ORC2 and ORC3 directly interacted with each other (FIG. 7). None of the other dual combinations of baculovirus showed any interaction under the experimental conditions. These findings indicate that ORC2 and ORC3 form a core component of the ORC2, 3, 4, 5 complex.

3. ORC2 and ORC3 Recruit ORC4 and 5

Figure 8:
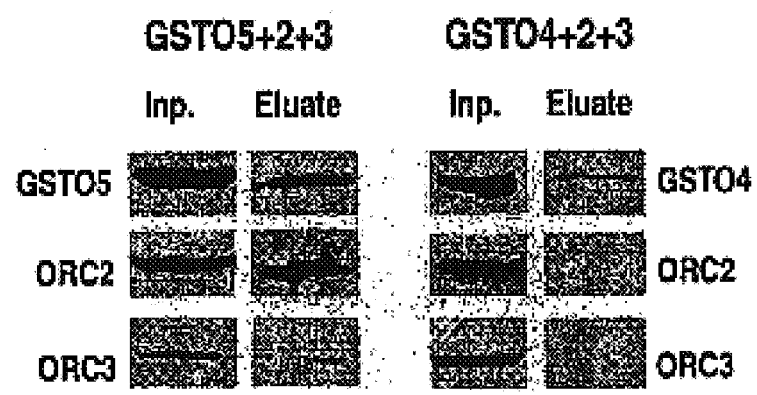
FIG. 8 shows immunoblots demonstrating that ORC2+3 subcomplex can load ORC5 but not ORC: Baculovirus-expressed GSTORC4+2+3 proteins bound to GST beads were immunoblotted using either anti-GST antibodies or respective anti-ORC antibodies. Input (Inp.) lane contains 5% of proteins input on GST beads.

The ORC2–3 complex is expected to recruit ORC4 and ORC5. To determine whether ORC2+3 core complex can recruit ORC4 first followed by ORC5 or vice versa, Sf9 cells were infected by baculoviruses expressing GSTORC4, 2 and 3 subunits or by viruses expressing GSTORC5, 2 and 3. GSTORC4 did not interact with ORC2 and ORC3 whereas GSTORC5 interacted with ORC2 and ORC3 (FIG. 8). This indicated that ORC2+3 core complex is capable of recruiting ORC5 but it cannot recruit ORC4 by itself. The fact that ORC2, 3, 4 and 5 form a complex suggests that ORC2, 3 and 5 complex is necessary to load ORC4. It is also possible that ORC4 and ORC5 can be loaded on ORC2+3 core complex simultaneously independent of each other but ORC5 is necessary to stabilize the association of ORC4 with the other ORC subunits.

4. N-terminal Portion of ORC3 Interacts with the C-terminal Portion of ORC2

Figure 9:
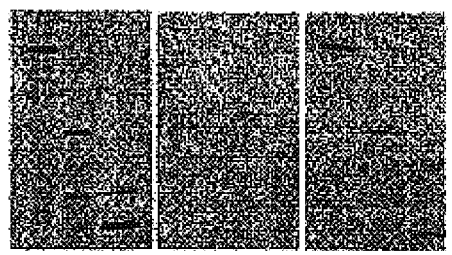
FIG. 9 shows bar graphs and immunoblots demonstrating the domains of interactions between ORC2 and ORC3.
Figure 9:
Figure 9:

Upon establishing the fact that ORC2 and ORC3 form a core complex, the interacting domains of ORC2 and ORC3 were mapped. N-terminal fragments of ORC3 labeled with $^{35}S$ methionine were produced by in vitro transcription and translation in rabbit reticulocyte lysate. The proteins were incubated with bacterially expressed and purified GSTORC2 protein. Three polypeptides derived from ORC3 were capable of binding GSTORC2 whereas the control GST protein did not bind any of them (FIG. 9A). The smallest fragment that bound to ORC2 contained 200 amino acids from the N-terminus of ORC3 (construct 3, ORC3N). To map the portion of ORC2 involved in the interaction with ORC3, GSTORC2C, containing the C-terminal 225 amino acids of ORC2 was expressed and purified. Both full-length ORC3, and ORC3N bound to GSTORC2C (FIG. 9B) whereas control GST alone did not bind to any one of them. Therefore, the C-terminal 225 residues of ORC2 interact with the N-terminal 200 residues of ORC3 to form the ORC2–3 complex at the core of human ORC. In the reciprocal deletion, removal of the first 200 amino acids of ORC3 abolished its ability to bind to GSTORC2 (FIG. 9C). These results indicate that the N-terminal 200 residues of ORC3 are necessary and sufficient to interact with ORC2.

5. N-terminal 200 Amino Acids of ORC3 can Compete with the Full Length ORC3.

Figure 10:
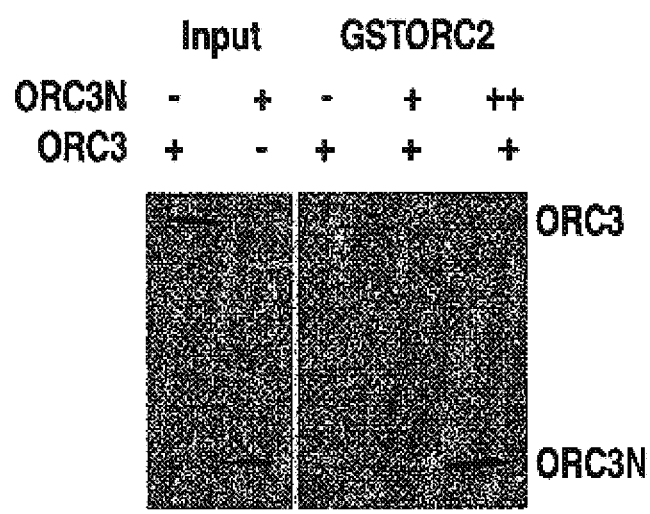
FIG. 10 shows an immunoblot demonstrating that ORC3N can compete with full-length ORC3. GSTORC2 beads were incubated with in vitro transcribed and translated full-length ORC3, then beads were thoroughly washed using binding buffer and incubated again with increasing amount of in vitro transcribed and translated ORC3N200. Beads were washed and bound labeled proteins were visualized by SDS-PAGE followed by fluorography.

Because the N-terminal 200 residues of ORC3 were determined to be sufficient for binding ORC2, its ability to compete with full length ORC3 for binding to GSTORC2 was investigated. $^{35}S$ methionine labeled ORC3 was bound to GSTORC2 beads under conditions where the latter was limiting. These beads were then incubated with increasing amount of ORC3N. The ORC3N protein was found to be able to compete with the full-length ORC3 protein for association with GSTORC2 (FIG. 10).

6. ORC3N Cannot Form a Complex that Contains ORC4+5

Figure 11:
FIG. 11 shows immunoblots demonstrating that ORC3N does not form a complex with ORC2, 4 and 5.

The ability of ORC3N to mediate the interaction of ORC2 with ORC4 and ORC5 was investigated. Sf9 insect cells were infected with baculoviruses expressing GSTORC5, ORC2, ORC4 and ORC3N. Following affinity purification on glutathione beads, and western blotting, the presence of GSTORC5 in the eluate from the beads was confirmed. Interestingly, in contrast to the result in FIG. 6A, none of the other ORC subunits came down with GSTORC5 although they were all present in the input lane at reasonable quantities (FIG. 11A). The physical interaction between ORC2 and ORC3N in the insect cell lysates was confirmed by co-immunoprecipitation reactions. The lysate was immuno-precipitated using either anti-ORC2 or anti-ORC3 antibodies followed by immunoblotting with both the antibodies. ORC2 was detected in anti-ORC3 immunoprecipitate and vice versa (FIG. 1B). Therefore, ORC3N was determined to be capable of interacting with ORC2 but this interaction was not sufficient for further binding of ORC4 and ORC5 under the conditions tested. The C-terminal portion of ORC3 appears to be important for binding of ORC4 and ORC5 subunits to ORC2+3 subcomplex under the conditions tested.

7. Expression of ORC3N in U2OS Cells Causes Cell Cycle Arrest

Figure 12:
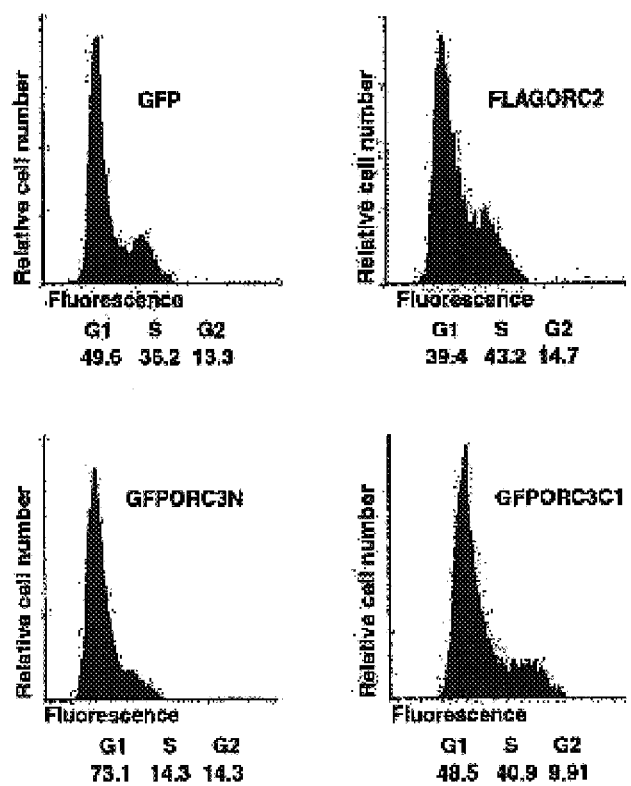
FIG. 12 shows graphs of FACS analysis of U2OS cells transfected with different constructs. U2OS cells were transfected either with farnesylated GFP (CLONTECH Laboratories, Inc., Palo Alto, Calif.) or in combination with FLAGORC2 or GFPORC3N or GFPORC3C 1. Transfected cells were fixed and stained with propidium iodide and then analyzed by FACS. Percentage of cell population present at different cell cycle stages in each transfection are shown at the bottom of the each panel.

Because ORC3N did not form a complex with ORC4 and ORC5 but still could interact with ORC2, ORC3N might show dominant negative effect on the cell cycle if overexpressed in a human cancer cell line. ORC3N and ORC3C1 were cloned into GFPC1 (CLONTECH Laboratories, Inc.) expression vector to produce non-farnesylated GFP fusion proteins. U2OS cells were transfected with plasmids expressing farnesylated GFP alone or in combination with FLAGORC2 or GFPORC3N or GFPORC3C1 (1:3 molar ratio) followed by FACS analysis after 48 hours. Cells transfected with GFP alone, FLAG-ORC2 or GFP-ORC3C1 showed normal cell cycle progression whereas cells transfected with GFP-ORC3N were blocked mostly in G1 (73%) (FIG. 12). This is the first evidence for any cell cycle effect of any human ORC protein. Because ORC3N can still bind ORC2 but not ORC4 and ORC5, it is possible that over expressed ORC3N interacts with ORC2 but prevents functional ORC formation. Consistent with this, over-expression of full length ORC3, which interacts with ORC2 but allows functional ORC formation did not block the cells in G1.

Example 3

Introduction

The ability of wild-type HCT116 cells and Δ/–HCT116 cells to support replication of pFS101 was examined to determine the effect of low levels of Orc2 on HPV replication.

Methods

The plasmid pFS101 (Sverdrup, F. M. et al., *Gene Therapy*, 6:1317–1321, 1999) is a 10.5 kb plasmid that contains the following elements:
1) Human papilloma virus-18 (HPV-18) E1 gene under control of a strong promoter from Rous sarcoma virus.
2) HPV-18 E2 gene under control of the long control region (LCR) from HPV-18.
3) The origin of replication of HPV-18 in the LCR.
4) A hygromycin-resistance marker gene under control of the promoter of Herpes Simplex virus thymidine kinase gene.

Two micrograms of this plasmid was transfected into Δ/–HCT116 cells (as described above) and wild type HCT116 cells in 10-cm plates with the cells at 50% confluency. The cells were put under hygromycin selection (100 μg/ml) 24 hrs after the transfection. The plates were fixed and stained with crystal violet on day 9.

Results

The presence of numerous hygromycin resistant colonies in wild-type HCT116 cells showed that these cells could support the replication of pFS101. Sverdrup, F. M. et al., *Gene Therapy* 6:1317–1321 (1999) showed that this replication is dependent on the HPV ori and the HPV replication initiators E1 and E2. The absence of similar hygromycin resistant colonies in Δ/–HCT116 cells showed that these cells, which express less than 10% of the wild-type levels of Orc2, could not support the replication of pFS 101.

As with the plasmids derived from the EBV ori, plasmids derived from HPV ori appeared to require normal levels of cellular ORC for their replication. Therefore, agents that inhibit the activity of ORC inhibit replication of HPV. In addition, agents like geminin that inhibit the replication initiation process begun by ORC also inhibit replication of HPV.

Example 4

Introduction

Fragments of geminin were tested to determine whether they inhibit replication from OriP of Epstein Barr virus.

Methods

Figure 13:
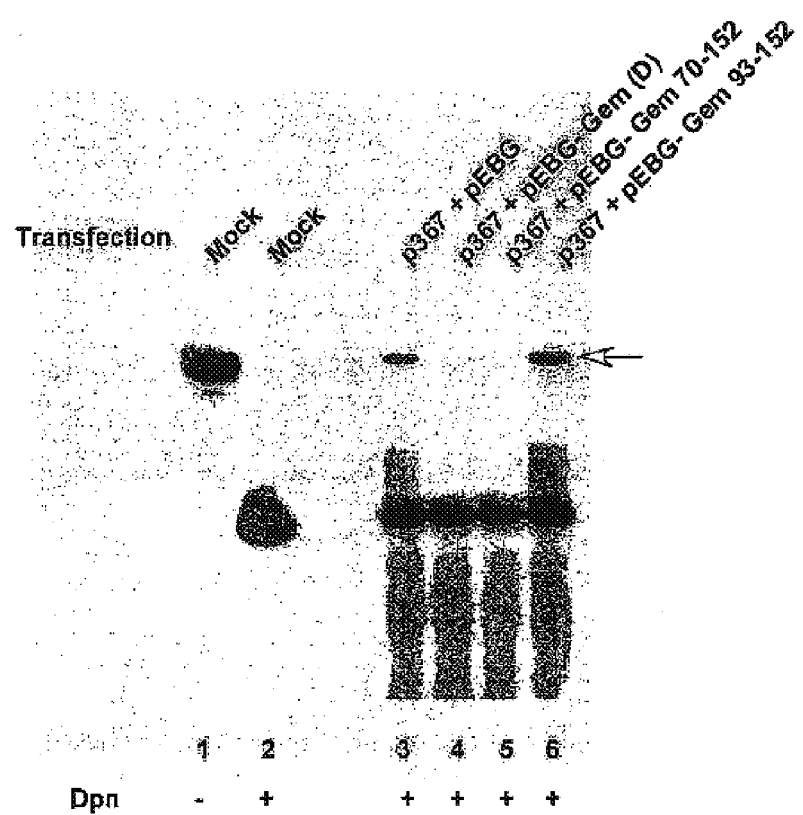
FIG. 13 shows a southern blot to detect DpnI-resistant p367 plasmids (containing oriP). GST-geminin destruction box mutant [pEBG-Gem (D)] is shown in lane 4. GST fused to residues 70–152 of geminin (pEBG-Gem 70–152) is shown in lane 5, and GST fused to residues 93–152 of geminin (pEBG-Gem 93–152) is shown in lane 6. The DpnI resistant (replicated) DNA is indicated by the arrow.

HCT116 cells were co-transfected with 1 μg of p367 (see Example 1) and 4 μg each of plasmids (pEBG) expressing GST (see FIG. 13, lane 3), GST-geminin destruction box mutant [pEBG-Gem (D); lane 4] or GST fused to residues 70–152 of geminin (pEBG-Gem 70–152 lane 5) or GST fused to residues 93–152 of geminin (pEBG-Gem 93–152). Plasmids were extracted by alkaline lysis 96 hr after transfection and digested with BamHI and DpnI (as indicated) before Southern blot. The DpnI resistant (replicated) DNA is shown in FIG. 13, and is indicated by the arrow.

Results

Results from the Southern blot indicated that DpnI-resistant plasmids (containing oriP) replicated in mammalian cells, but in plasmids that expressed GST fused to residues 70–152 of geminin did not replicate. This indicated that the fragment that includes amino acids 70–152 of geminin inhibited replication from oriP of EBV.

Each of the above-identified references, patents/patent publications is incorporated in its entirety herein by reference. The preceding is merely a detailed description of certain preferred embodiments. It therefore should be apparent to those skilled in the art that various modifications and equivalents can be made without departing from the spirit or scope of the invention.

We claim:

1. A method for treating a viral infection in a subject who is otherwise free of indications for geminin treatment comprising:
administering to the subject who is otherwise free of indications for geminin treatment a therapeutically effective amount of a geminin nucleic acid molecule that encodes a geminin polypeptide, to treat the viral infection in the subject wherein the geminin nucleic acid molecule is SEQ ID NO: 1; or SEQ ID NO: 9; or degenerates thereof.

2. The method of claim 1, wherein the viral infection is an infection with a virus that replicates as episomes in cells.

3. The method of claim 2, wherein the cells are human cells.

4. The method of claim 1, wherein the viral infection is selected from the group consisting of: herpesvirus infection, papillomavirus infection, and polyomavirus infection.

5. The method of claim 1, wherein the viral infection is a herpesvirus infection selected from the group consisting of: Epstein Barr Virus (EBV), Herpes Simplex Virus 1, Herpes Simplex Virus 2, varicella zoster, cytomegalovirus, rhadinovirus, and roseolovirus.

6. The method of claim 1, wherein the viral infection is Epstein-Barr virus (EBV).

7. The method of claim 1, wherein the viral infection is a latent EBV infection of human epithelial cells and/or B cells.

8. The method of claim 1, wherein the subject is a human.

9. The method of claim 1, wherein the subject is immunocompromised.

10. The method of claim 1, wherein the subject is immunocompetent.

* * * * *

SEQUENCE LISTING

<160> NUMBER OF SEQ ID NOS: 17

<210> SEQ ID NO 1
<211> LENGTH: 630
<212> TYPE: DNA
<213> ORGANISM: Homo sapiens

<400> SEQUENCE: 1

```
atgaatccca gtatgaagca gaaacaagaa gaaatcaaag agaatataaa gaatagttct      60
gtcccaagaa gaactctgaa gatgattcag ccttctgcat ctggatctct tgttggaaga     120
gaaaatgagc tgtccgcagg cttgtccaaa aggaaacatc ggaatgacca cttaacatct     180
acaacttcca gccctggggt tattgtccca gaatctagtg aaaataaaaa tcttggagga     240
gtcacccagg agtcatttga tcttatgatt aaagaaaatc catcctctca gtattggaag     300
gaagtggcag aaaaacggag aaaggcgctg tatgaagcac ttaaggaaaa tgagaaactt     360
cataaagaaa ttgaacaaaa ggacaatgaa attgcccgcc tgaaaaagga gaataagaa      420
```

```
ctggcagaag tagcagaaca tgtacagtat atggcagagc taatagagag actgaatggt    480
gaacctctgg ataattttga atcactggat aatcaggaat ttgattctga agaagaaact    540
gttgaggatt ctctagtgga agactcagaa attggcacgt gtgctgaagg aactgtatct    600
tcctctacgg atgcaaagcc atgtatatga                                      630
```

<210> SEQ ID NO 2
<211> LENGTH: 209
<212> TYPE: PRT
<213> ORGANISM: Homo sapiens

<400> SEQUENCE: 2

```
Met Asn Pro Ser Met Lys Gln Lys Gln Glu Glu Ile Lys Glu Asn Ile
1               5                   10                  15

Lys Asn Ser Ser Val Pro Arg Arg Thr Leu Lys Met Ile Gln Pro Ser
                20                  25                  30

Ala Ser Gly Ser Leu Val Gly Arg Glu Asn Glu Leu Ser Ala Gly Leu
            35                  40                  45

Ser Lys Arg Lys His Arg Asn Asp His Leu Thr Ser Thr Thr Ser Ser
        50                  55                  60

Pro Gly Val Ile Val Pro Glu Ser Ser Glu Asn Lys Asn Leu Gly Gly
65                  70                  75                  80

Val Thr Gln Glu Ser Phe Asp Leu Met Ile Lys Glu Asn Pro Ser Ser
                85                  90                  95

Gln Tyr Trp Lys Glu Val Ala Glu Lys Arg Arg Lys Ala Leu Tyr Glu
            100                 105                 110

Ala Leu Lys Glu Asn Glu Lys Leu His Lys Glu Ile Glu Gln Lys Asp
        115                 120                 125

Asn Glu Ile Ala Arg Leu Lys Lys Glu Asn Lys Glu Leu Ala Glu Val
    130                 135                 140

Ala Glu His Val Gln Tyr Met Ala Glu Leu Ile Glu Arg Leu Asn Gly
145                 150                 155                 160

Glu Pro Leu Asp Asn Phe Glu Ser Leu Asp Asn Gln Glu Phe Asp Ser
                165                 170                 175

Glu Glu Glu Thr Val Glu Asp Ser Leu Val Glu Asp Ser Glu Ile Gly
            180                 185                 190

Thr Cys Ala Glu Gly Thr Val Ser Ser Ser Thr Asp Ala Lys Pro Cys
        195                 200                 205

Ile
```

<210> SEQ ID NO 3
<211> LENGTH: 603
<212> TYPE: DNA
<213> ORGANISM: Homo sapiens

<400> SEQUENCE: 3

```
atgaatccca gtatgaagca gaaacaagaa gaaatcaaag agaatataaa gaatagttcg     60
gtaccatctg catctggatc tcttgttgga agagaaaatg agctgtccgc aggcttgtcc    120
aaaaggaaac atcggaatga ccacttaaca tctacaactt ccagccctgg ggttattgtc    180
ccagaatcta gtgaaaataa aaatcttgga ggagtcaccc aggagtcatt tgatcttatg    240
attaaagaaa atccatcctc tcagtattgg aaggaagtgg cagaaaaacg agaaaggcg     300 ctgtatgaag cacttaagga aaatgagaaa cttcataaag aaattgaaca aaaggacaat    360
gaaattgccc gcctgaaaaa ggagaataaa gaactggcag aagtagcaga acatgtacag    420
```

-continued

| | |
|---|---|
| tatatggcag agctaataga gagactgaat ggtgaacctc tggataattt tgaatcactg | 480 |
| gataatcagg aatttgattc tgaagaagaa actgttgagg attctctagt ggaagactca | 540 |
| gaaattggca cgtgtgctga aggaactgta tcttcctcta cggatgcaaa gccatgtata | 600 |
| tga | 603 |

<210> SEQ ID NO 4
<211> LENGTH: 200
<212> TYPE: PRT
<213> ORGANISM: Homo sapiens

<400> SEQUENCE: 4

Met Asn Pro Ser Met Lys Gln Lys Gln Glu Glu Ile Lys Glu Asn Ile
1               5                   10                  15

Lys Asn Ser Ser Val Pro Ser Ala Gly Ser Leu Val Gly Arg Glu
            20                  25                  30

Asn Glu Leu Ser Ala Gly Leu Ser Lys Arg Lys His Arg Asn Asp His
        35                  40                  45

Leu Thr Ser Thr Thr Ser Ser Pro Gly Val Ile Val Pro Glu Ser Ser
    50                  55                  60

Glu Asn Lys Asn Leu Gly Gly Val Thr Gln Glu Ser Phe Asp Leu Met
65                  70                  75                  80

Ile Lys Glu Asn Pro Ser Ser Gln Tyr Trp Lys Glu Val Ala Glu Lys
                85                  90                  95

Arg Arg Lys Ala Leu Tyr Glu Ala Leu Lys Glu Asn Glu Lys Leu His
            100                 105                 110

Lys Glu Ile Glu Gln Lys Asp Asn Glu Ile Ala Arg Leu Lys Lys Glu
        115                 120                 125

Asn Lys Glu Leu Ala Glu Val Ala Glu His Val Gln Tyr Met Ala Glu
    130                 135                 140

Leu Ile Glu Arg Leu Asn Gly Glu Pro Leu Asp Asn Phe Glu Ser Leu
145                 150                 155                 160

Asp Asn Gln Glu Phe Asp Ser Glu Glu Thr Val Glu Asp Ser Leu
                165                 170                 175

Val Glu Asp Ser Glu Ile Gly Thr Cys Ala Glu Gly Thr Val Ser Ser
            180                 185                 190

Ser Thr Asp Ala Lys Pro Cys Ile
        195                 200

<210> SEQ ID NO 5
<211> LENGTH: 600
<212> TYPE: DNA
<213> ORGANISM: Homo sapiens

<400> SEQUENCE: 5

| | |
|---|---|
| atggctacgt cctcgatgtc taagggttgc tttgttttta agccaaactc caaaaagaga | 60 |
| aagatctctc tgccaataga ggactatttt aacaaaggga aaatgagcc tgaggacagt | 120 |
| aagcttcgat tcgaaactta tcagttgata tggcagcaga tgaaatctga aaatgagcga | 180 |
| ctacaagagg aattaaataa aaacttgttt gacaatctga ttgaatttct gcaaaaatca | 240 |
| cattctggat tccagaagaa ttcaagagac tgggcggtc aaataaaact cagagaaatt | 300 |
| ccaactgctg ctcttgttct tggtgtgaat gtcacagatc atgatttgac attcggaagt | 360 |
| ctaacagagg cccttcagaa taatgtcaca ccatatgtag tctcattgca agctaaagat | 420 |
| tgtccagata tgaaacattt tttgcaaaag ttgatctcac agttgatgga ctgctgtgta | 480 |

```
gatataaaat ccaaagagga ggaaagtgtt cacgtcaccc aaagaaagac acattattca      540
atggattcac tttccagttg gtatatgact gtcacacaga agacggaccc aaaaatgcta      600
```

<210> SEQ ID NO 6
<211> LENGTH: 200
<212> TYPE: PRT
<213> ORGANISM: Homo sapiens

<400> SEQUENCE: 6

```
Met Ala Thr Ser Ser Met Ser Lys Gly Cys Phe Val Phe Lys Pro Asn
1               5                   10                  15

Ser Lys Lys Arg Lys Ile Ser Leu Pro Ile Glu Asp Tyr Phe Asn Lys
            20                  25                  30

Gly Lys Asn Glu Pro Glu Asp Ser Lys Leu Arg Phe Glu Thr Tyr Gln
        35                  40                  45

Leu Ile Trp Gln Gln Met Lys Ser Glu Asn Glu Arg Leu Gln Glu Glu
    50                  55                  60

Leu Asn Lys Asn Leu Phe Asp Asn Leu Ile Glu Phe Leu Gln Lys Ser
65                  70                  75                  80

His Ser Gly Phe Gln Lys Asn Ser Arg Asp Leu Gly Gly Gln Ile Lys
                85                  90                  95

Leu Arg Glu Ile Pro Thr Ala Ala Leu Val Leu Gly Val Asn Val Thr
            100                 105                 110

Asp His Asp Leu Thr Phe Gly Ser Leu Thr Glu Ala Leu Gln Asn Asn
        115                 120                 125

Val Thr Pro Tyr Val Val Ser Leu Gln Ala Lys Asp Cys Pro Asp Met
    130                 135                 140

Lys His Phe Leu Gln Lys Leu Ile Ser Gln Leu Met Asp Cys Cys Val
145                 150                 155                 160

Asp Ile Lys Ser Lys Glu Glu Glu Ser Val His Val Thr Gln Arg Lys
                165                 170                 175

Thr His Tyr Ser Met Asp Ser Leu Ser Ser Trp Tyr Met Thr Val Thr
            180                 185                 190

Gln Lys Thr Asp Pro Lys Met Leu
        195                 200
```

<210> SEQ ID NO 7
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 7

```
agctaccttg attggattta gctc                                              24
```

<210> SEQ ID NO 8
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 8

```
acctccttct ctatctagaa tgtg                                              24
```

<210> SEQ ID NO 9
<211> LENGTH: 249
<212> TYPE: DNA
<213> ORGANISM: Homo sapiens

<400> SEQUENCE: 9

```
ccagaatcta gtgaaaataa aaatcttgga ggagtcaccc aggagtcatt tgatcttatg      60
attaaagaaa atccatcctc tcagtattgg aaggaagtgg cagaaaaacg gagaaaggcg     120
ctgtatgaag cacttaagga aaatgagaaa cttcataaag aaattgaaca aaaggacaat     180
gaaattgccc gcctgaaaaa ggagaataaa gaactggcag aagtagcaga acatgtacag     240
tatatggca                                                             249
```

<210> SEQ ID NO 10
<211> LENGTH: 83
<212> TYPE: PRT
<213> ORGANISM: Homo sapiens

<400> SEQUENCE: 10

```
Pro Glu Ser Ser Glu Asn Lys Asn Leu Gly Gly Val Thr Gln Glu Ser
1               5                   10                  15
Phe Asp Leu Met Ile Lys Glu Asn Pro Ser Ser Gln Tyr Trp Lys Glu
            20                  25                  30
Val Ala Glu Lys Arg Arg Lys Ala Leu Tyr Glu Ala Leu Lys Glu Asn
        35                  40                  45
Glu Lys Leu His Lys Glu Ile Glu Gln Lys Asp Asn Glu Ile Ala Arg
    50                  55                  60
Leu Lys Lys Glu Asn Lys Glu Leu Ala Glu Val Ala Glu His Val Gln
65                  70                  75                  80
Tyr Met Ala
```

<210> SEQ ID NO 11
<211> LENGTH: 24
<212> TYPE: PRT
<213> ORGANISM: Homo sapiens

<400> SEQUENCE: 11

```
Pro Glu Ser Ser Glu Asn Lys Asn Leu Gly Gly Val Thr Gln Glu Ser
1               5                   10                  15
Phe Asp Leu Met Ile Lys Glu Asn
            20
```

<210> SEQ ID NO 12
<211> LENGTH: 29
<212> TYPE: PRT
<213> ORGANISM: Homo sapiens

<400> SEQUENCE: 12

```
Pro Glu Ser Ser Glu Asn Lys Asn Leu Gly Gly Val Thr Gln Glu Ser
1               5                   10                  15
Phe Asp Leu Met Ile Lys Glu Asn Pro Ser Ser Gln Tyr
            20                  25
```

<210> SEQ ID NO 13
<211> LENGTH: 32
<212> TYPE: PRT
<213> ORGANISM: Homo sapiens

```
<400> SEQUENCE: 13

Pro Glu Ser Ser Glu Asn Lys Asn Leu Gly Gly Val Thr Gln Glu Ser
1               5                   10                  15

Phe Asp Leu Met Ile Lys Glu Asn Pro Ser Ser Gln Tyr Trp Lys Glu
            20                  25                  30

<210> SEQ ID NO 14
<211> LENGTH: 29
<212> TYPE: PRT
<213> ORGANISM: Homo sapiens

<400> SEQUENCE: 14

Pro Gly Val Ile Val Pro Glu Ser Ser Glu Asn Lys Asn Leu Gly Gly
1               5                   10                  15

Val Thr Gln Glu Ser Phe Asp Leu Met Ile Lys Glu Asn
            20                  25

<210> SEQ ID NO 15
<211> LENGTH: 36
<212> TYPE: PRT
<213> ORGANISM: Homo sapiens

<400> SEQUENCE: 15

Leu Thr Ser Thr Thr Ser Ser Pro Gly Val Ile Val Pro Glu Ser Ser
1               5                   10                  15

Glu Asn Lys Asn Leu Gly Gly Val Thr Gln Glu Ser Phe Asp Leu Met
            20                  25                  30

Ile Lys Glu Asn
        35

<210> SEQ ID NO 16
<211> LENGTH: 34
<212> TYPE: PRT
<213> ORGANISM: Homo sapiens

<400> SEQUENCE: 16

Pro Gly Val Ile Val Pro Glu Ser Ser Glu Asn Lys Asn Leu Gly Gly
1               5                   10                  15

Val Thr Gln Glu Ser Phe Asp Leu Met Ile Lys Glu Asn Pro Ser Ser
            20                  25                  30

Gln Tyr

<210> SEQ ID NO 17
<211> LENGTH: 41
<212> TYPE: PRT
<213> ORGANISM: Homo sapiens

<400> SEQUENCE: 17

Leu Thr Ser Thr Thr Ser Ser Pro Gly Val Ile Val Pro Glu Ser Ser
1               5                   10                  15

Glu Asn Lys Asn Leu Gly Gly Val Thr Gln Glu Ser Phe Asp Leu Met
            20                  25                  30

Ile Lys Glu Asn Pro Ser Ser Gln Tyr
        35                  40
```